US008512714B2

(12) United States Patent
Mikkelsen et al.

(10) Patent No.: US 8,512,714 B2
(45) Date of Patent: Aug. 20, 2013

(54) THERMOANAEROBACTER MATHRANII STRAIN BG1

(75) Inventors: Marie Just Mikkelsen, Bronshoj (DK); Birgitte Kiaer Ahring, Horsholm (DK); Tania Ivanova Georgieva, Gentofte (DK)

(73) Assignee: BioGasol IPR ApS, Ballerup (DK)

( * ) Notice: Subject to any disclaimer, the term of this patent is extended or adjusted under 35 U.S.C. 154(b) by 680 days.

(21) Appl. No.: 12/301,687

(22) PCT Filed: May 22, 2007

(86) PCT No.: PCT/DK2007/000241
§ 371 (c)(1),
(2), (4) Date: Nov. 20, 2008

(87) PCT Pub. No.: WO2007/134607
PCT Pub. Date: Nov. 29, 2007

(65) Prior Publication Data
US 2010/0143988 A1 Jun. 10, 2010

(30) Foreign Application Priority Data

May 22, 2006 (DK) .................................. 2006 00703

(51) Int. Cl.
*A61K 39/02* (2006.01)
*C12P 7/06* (2006.01)
*G01N 33/00* (2006.01)

(52) U.S. Cl.
USPC ...... 424/234.1; 424/93.1; 424/94.1; 435/161; 436/132

(58) Field of Classification Search
USPC .................. 424/234.1, 93.1, 94.1; 435/161; 436/132
See application file for complete search history.

(56) References Cited

U.S. PATENT DOCUMENTS

| 6,555,350 B2 | 4/2003 | Ahring et al. |
| 8,236,547 B2 | 8/2012 | Mikkelsen et al. |

FOREIGN PATENT DOCUMENTS

| JP | 2004-344107 A | 9/2004 |
| RU | 2278160 C2 | 6/2006 |
| WO | 01/21825 A2 | 3/2001 |
| WO | 03/000913 A2 | 3/2003 |
| WO | 2006-117536 A1 | 9/2006 |
| WO | 2007053600 A3 | 5/2007 |
| WO | 2007-115228 A2 | 10/2007 |
| WO | 2007-134607 A1 | 11/2007 |
| WO | 2008-006037 A2 | 1/2008 |

OTHER PUBLICATIONS

Benson, D.A. et al. "GenBank." Nucleic Acids Research, vol. 33, Database Issue, D34-D38. (2005), Oxford University Press.
Bryant, F.O. "Characterization of the fructose 1, 6-bisphosphate-activated, L(+)-lactate dehydrogenase from *Thermoanarobacter ethanolicus*." J Enzyme Inhib. 5, 235-248 (1991), Harwood Academic Publishers GmbH.
Burdette, D.S. et al. "Physiological function of alcohol dehydrogenases and long-chain (C(30)j) fatty acids in alcohol tolerance of *Thermoanaerobacter ethanolicus*," Applied and Environ. Microbiol., vol. 68, No. 4, pp. 1914-1918. (2002).
Carreira, L.H. "Control of product formation with *Thermoanaerobacter ethanolicus*, enzymology and physiology." In Genetics of Industrial Microorganisms, Y.Ikeda, ed. American Society for Microbiology, Washington D.C., pp. 351-355 (1962).
Collins, M.D. et al. "The phylogeny of the genus Clostridium: proposal of five new genera and eleven new species combinations." Int J. Cyst. Bacteriol., vol. 44. No. 4, pp. 812-826. (1994).
Cook, G.M. "The intracellular pH of the thermophilic bacterium *Thermoanaerobacter wiegelii*during growth and production of fermentation acids." Extremophilies 4. 279-284. (2000).
Dien, B.S. et al. "Development of new ethanologenic *Escherichia coli* strains for fermentation of lignocellulosic biomass." Appl Biochem. and Biotechnol., vol. 84-85, pp. 181-196. (2000).
Erbeznik, M. et al. Cloning and characterization of transcription of the xyIAB operon in *Thermoanaerobacter ethanolicus*. J. Bacteriol., vol. 180, No. 5, pp. 1103-1109. (1998).
Herrero, A.A. et al. "Development of ethanol tolerance in *Clostridium thermocellum*: effect of growth temperature." Appl. Environ. Microbiol., vol. 40, No. 3, pp. 571-577. (1980).
Ho, N.W. et al. "Genetically engineered *Saccharomyces* yeast capable of effective cofermentation of glucose and xylose." Appl. Environ. Microbiol., vol. 64, No. 5, pp. 1852-1859. (1998).
Hueck, C.J. et al. "Catabolite repression in *Bacillus subtillis*: a global regulatory mechanism for the gram-positive bacteria?" Mol. Microbiol., vol. 15(3), pp. 395-401. (1995), Blackwell Publishing Limited.
Klinke, H.B. et al. "Inhibition of ethanol-producing yeast and bacteria by degradation products produced during pre-treatment of biomass." Appl. Microbiol. Biotechnol. 66, 10-26. (2004), Springer-Verlag.
Kumar, S. et al. "MEGA2: molecular evolutionary genetics analysis software." Bioinformatics., vol. 17, No. 12 2001, pp. 1244-1245. (2001).
Lamed, R. et al. "Ethanol production by thermophillic bacteria: relationship between fermentation product yields of and catabolic enzyme activities in *Clostridium thermocellum* and *Thermoanaerobium brockii*." J. Bacteriol 144, 569-578. (1980).
Larsen, L. et al. "*Thermoanaerobacter mathranii*sp nov, an ethanol-producing, extremely thermophilic anarobic bacterium from a hot spring in Iceland." Arch. Microbiol. 168, 114-119, (1997), Springer-Verlag.
Lawford, H.G. et al. "Performance testing of *Zymomonas mobilis* metabolically engineered for cofermentation of glucose, xylose and arabinose." Appl. Biochem. and Biotechnol., vols. 98-100, 429-448, (2002), Humana Press Inc.

(Continued)

Primary Examiner — Rodney P. Swartz
(74) Attorney, Agent, or Firm — Robert Mlotkowski Safran & Cole, P.C.

(57) ABSTRACT

Strict anaerobic thermophilic bacterium belonging to the group of *Thermoanaerobacter mathranii* and mutants and derivatives thereof. The bacterium is particularly suitable for the production of fermentation products such as ethanol, lactic acid, acetic acid and hydrogen from lignocellulosic biomass.

24 Claims, 21 Drawing Sheets

(56) References Cited

OTHER PUBLICATIONS

Figure 1:
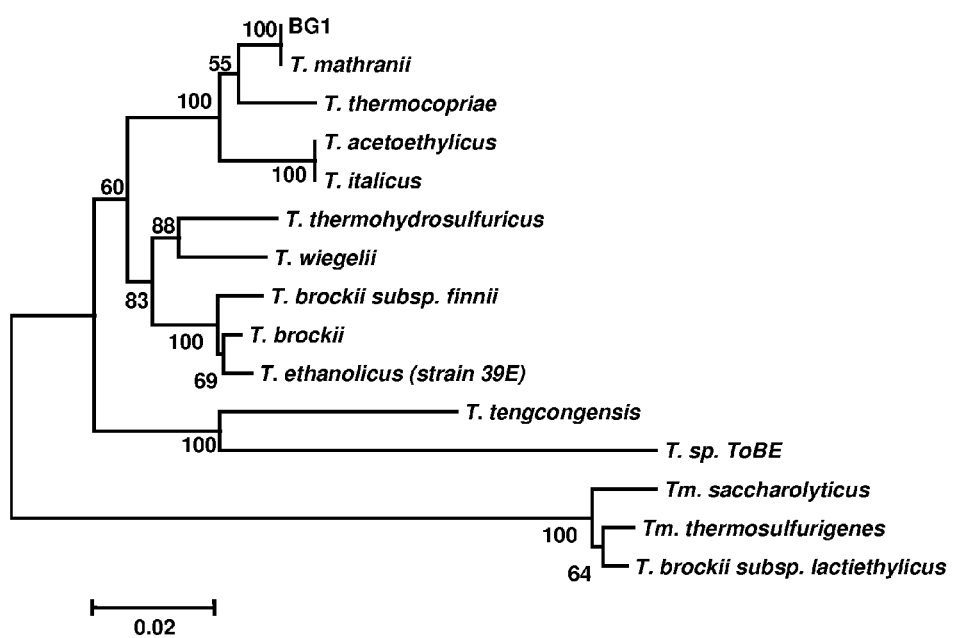

Lovitt, R.W. et al. "Ethanol-Production by Thermophilic Bacteria: Physiological Comparison of Solvent Effects on Parent and Alcohol-Tolerant Strains of Clostridium-Thermohydrosulfuricum." Appl. Environ. Microbiol. 48, 171-177. (1984).
Lovitt, R.W. et al. "Ethanol-Production by Thermophilic Bacteria—Biochemical Basis for Ethanol and Hydrogen Tolerance in Clostridium-Thermohydrosulfuricum". J. of Bacteriol., vol. 170, No. 6, pp. 2809-2815. (1988).
Lynd, L.R. "Production of ethanol from lignocellulosic materials using thermophilic bateria. Critical evaluation of potential and review." Advances in Biochemical Engineering/Biotechnology, vol. 38, pp. 1-52, (1989), (New York: Springer Verlag).
Rani, K.S. et al. "High ethanol tolerance of new isolates of *Clostridium thermocellum* strains SS21 and SS22." World J. of Microbiol. & Biotechnol., vol. 15, pp. 173-178. (1999).
Rani, K.S. et al. "Improved ethanol tolerance and production in strains of *Clostridium thermocellum*." World J. of Microbiol. & Biotechnol., vol. 12, pp. 57-60. (1996).
Saddler, J.N. et al. "Coversion of pretreated lignocellulosic substrates to ethanol by *Clostridium thermocellum* in mono- and co- culture with *Clostridium thermosaccharolyticum* and *Clostridium thermohydrosulfuricum*." Can J. Microbiol., vol. 30, pp. 212-220. (1984).
Wiegel, J. et al. "*Thermoanaerobacter ethanolicus*gen. nov. spec. nov., a new, extreme thermophilic, anaerobic bacterium." Arch Microbiol 128, 343-348. (1981).
Von Sivers et al. "Cost analysis of ethanol production from willow using recombinant *Escherichia coli*." Biotechnol. Prog., 1994, vol. 10, p. 555-560. (1994).
Hungate R.E. "A roll tube method for cultivation of strict anaerobes." Chapter IV—p. 117-132. (1969) Department of Bacteriology, University of California, Davis, California.
Bryant M.P. "Commentary on the Hungate technique for culture of anaerobic bacteria." The American Journal of Clinical Nutrition. vol. 25, pp. 1324-1328. (1972).
Hoseki et al. "Directed Evolution of Thermostable Kanamycin-Resistance Gene: A covenient Selection Marker for *Thermus thermophilus1*", J. Biochem. vol. 126, pp. 951-956. (1999).
Lynd et al. "Salt accumulation resulting from base added for pH control, and not ethanol, limits growth of *Thermoanaerobacterium thermosaccharolyticum* HG-8 at elevated feed xylose concentrations in continuous culture." Biotechnol. Prog., vol. 17, p. 118-125. (2001).
Palmqvist, E. et al. "Fermentation of lignocellulosic hydrolysates. I: inhibition and detoxification." Bioresource Technology. vol. 74. p. 17-24. (2000)
Zalvidar et al., Fuel ethanol production from lignocellulose: a challenge for metabolic engineering and process integration, Appl. Microbiol. Biotechnol. vol. 56., p. 17-34, (2001).
Desai S.G. et al. "Cloning of L-lactate dehydrogenase and elimination of lactic acid production via gene knockout in *Thermoanaerobacterium saccharolyticum* JW/SL-YS485." Applied Microbiology and Biotechnology. Berlin, vol. 65., pp. 600-605. (2004).
Mayer, M.A. et al. "Isolation and properties of acetate kinase- and phosphotransacetylase-negative mutants of *Thermoanaerobacter thermohydrosulfuricus*." Microbiology, Society for General Microbiology. vol. 141. No. 11, pp. 2891-2896. (1995) Great Britain.
Ahring, B.K. et al., "Production of ethanol from wet oxidised wheat straw by *Thermoanaerobacter mathranii*," Bioresource Technology, vol. 68, p. 3-9, (1999).
Carlier, JP et al., "Isolation from canned foods of a novel *Thermoanaerobacter* species phylogenetically related to *Thermoanaerobacter mathranii* (Larsen1997): Emendation of the species description and proposal of *Thermoanaerobacter mathranii* subsp. *Alimentarius* subsp. Nov", Anaerobe, vol. 12, pp. 153-149, (2006).
Xue, Y et al., "*Thermoanaerobacter tengcongenesis* sp. nov., a novel anaerobic, saccharolytic, thermophilic bacterium isolated from a hot spring in Tengcong, China", International Journal of Systematic and Evolutionary Microbiology, vol. 51, pp. 1335-1341, (2001).
National Centre of the Intellectual Property "Sakpatenti" of Georgia, Search Report, (Sep. 21, 2009).
Carlos Martin et al. "Comparison of the resistance of industrial and laboratory strains of *Saccharomyces* and *Zygosaccharomyces* to lignocellulose-derived fermentation inhibitors" Enzyme and Microbial Technology 32 (2003) 386-395.
Hild et al., Effect of nutrient limitation on product formation during continuous fermentation of xylose with *Thermoanaerobacter ethanolicus*JW200 Fe(7), Appl Microbiol Biotechnol, Dec. 19, 2002, 60:679-686.
Basem Soboh et al., A multisubunit membrane-bound [NiFe] hydrogenase and an NADH-dependent Fe-only hydrogenase in the fermenting bacterium *Thermoanaerobacter tengcongensis*, Microbiology (2004), 150, 2451-2463.
Berrios-Rivera et al., "The Effect of NAPRTase Overexpression on the Total Levels of NAD, The NADH/NAD+ Ratio, and the Distribution of Metabolites in *Escherichia coli*", Metabolic Engineering Academic Press, US, vol. 4. pp. 238-247, 2002.
Berrios-Rivera et al., "The effect of carbon sources and lactate dehydrogenase deletion on 1,2-propanediol production in *Escherichia coli*", J. Ind Microbiol Biotechnol, vol. 30, pp. 34-40, 2003.
Bradford, M.M., "A Rapid and Sensitive Method for the Quantitation of Microgram Quantities of Protein Utilizing the Principle of Protein-dye Binding", Analytical Biochemistry, vol. 72, pp. 248-254, 1976.
Brinen et al., "Crystal Structure of a Zinc-containing Glycerol Dehydrogenase (TM0423) from *Thermotoga marilima* at 1.5 ANG Resolution", Proteins, vol. 50, No. 2, pp. 371-374, 2002.
Burton, R. M. (Colowick et al.), "Methods in Enzymology", vol. 1, pp. 397-401, 1955.
Bjerre et al., "Pretreatment of Wheat Straw Using Combined Wet Oxidation and Alkaline Hydrolysis Resulting in Convertible Cellulose and Hemicellulose", Biotechnology and Bioengineering, vol. 49, pp. 568-577, 1996.
Gonzalez-Pajuelo et al., "Microbial Conversion of Glycerol to 1,3-Propanediol: Physiological Comparison of a Natural Producer, Clostridium bulyricum VPI 3266, and an Engineered Strain, *Clostridium acetobutylicum* DG1(pSPD5)", Applied and Environment Microbiology, vol. 72, No. 1, pp. 96-101, 2006.
Ruzheinikov, S.N. et al. "Glycerol Dehydrogenase: Structure, Specificity, and Mechanism of a Family III Polyol Dehydrogenase", Structure, vol. 9, pp. 789-802. Sep. 2001.
Vasconcelos et al., "Regulation of Carbon and Electron Flow in *Clostridium acetobutylicum* Grown in Chemostat Culture at Neutral pH on Mixtures of Glucose and Glycerol", Journal of Bacteriology, vol. 176, No. 3, pp. 1443-1450, 1994.
Yazdani, S. S. et al., "Engineering *Eschrichia coli* for the efficient conversion of glycerol to ethanol and co-products," Metabolic Engineering, Academic Press, US, vol. 10, No. 6, pp. 340-351, 2008.
Yazdani et al., "Engineering *Eschrichia coli* for the efficient conversion of glycerol to ethanol and co-products,"30th Annual Symposium on Biotechnology for Fuels and Chemicals, pp. No. 40 and 54, May 2008.
International Preliminary Report on Patentability in corresponding PCT/EP2009/059421 dated Oct. 4, 2010.
International Search Report in corresponding PCT/EP2009/059421 dated Oct. 9, 2009.
U.S. Appl. No. 13/055,079; Published as U.S. Pub. No. 2011/0287501A1; Patented as U.S. Patent No. 8,236,547 B2.

B

| Strain | BG1 | | | BG1L1 | | |
|---|---|---|---|---|---|---|
| Glucose g/l | 2.21 | 4.48 | 8.89 | 2.02 | 4.67 | 9.06 |
| C rec | 1.04 | 0.97 | 0.94 | 1.06 | 0.99 | 0.99 |

Fig. 10

| | Influent | | Effluent | | | | $C_{TS}$ | $Y_{Ace/TS}$ | $Y_{EtOH/TS}$ | $Y^*_{EtOH/TS}$ | $Q_{EtOH}$ | CR |
|---|---|---|---|---|---|---|---|---|---|---|---|---|
| HRT | Glu | Xyl | Glu | Xyl | Ace | EtOH | | | | | | |
| hours | g/l | g/l | g/l | g/l | g/l | g/l | % | g/g | g/g | g/g | g/l/h | % |
| 8 | 0 | 10,29 | 0 | 0,12 | 0,34 | 4,07 | 98,8 | 0,03 | 0,4 | 0,45 | 0,51 | 0,83 |
| 8 | 10,86 | 9,65 | 0,02 | 0,24 | 1,4 | 6,43 | 98,7 | 0,07 | 0,31 | 0,41 | 0,8 | 0,73 |
| 8 | 19,29 | 9,41 | 2,06 | 1,76 | 2,23 | 7,4 | 86,7 | 0,08 | 0,26 | 0,34 | 0,93 | 0,72 |
| 24 | 20,42 | 9,77 | 0 | 0,09 | 2,68 | 10,35 | 99,7 | 0,09 | 0,34 | 0,40 | 0,43 | 0,81 |
| 24 | 25,23 | 14,64 | 0,12 | 0,47 | 3,19 | 13,2 | 98,9 | 0,08 | 0,33 | 0,40 | 0,55 | 0,78 |
| 24 | 33,11 | 21,39 | 3,37 | 1,74 | 4,49 | 15,35 | 90,6 | 0,08 | 0,28 | 0,36 | 0,64 | 0,74 |
| 24 | 40,55 | 24,71 | 14,05 | 6,38 | 2,43 | 10,46 | 68,7 | 0,04 | 0,16 | 0,28 | 0,44 | 0,54 |

Fig. 13
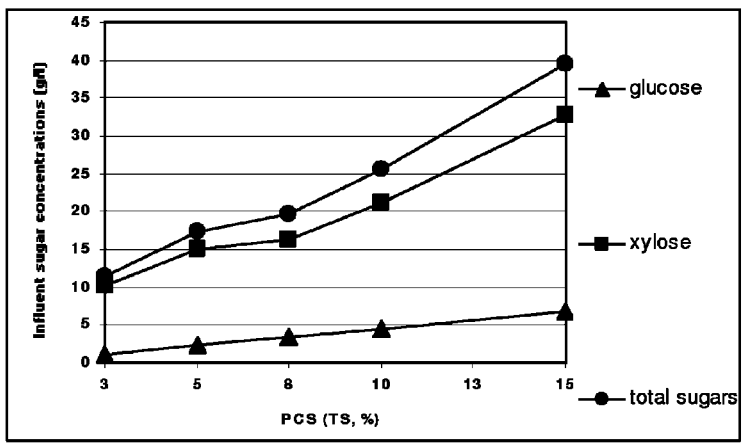
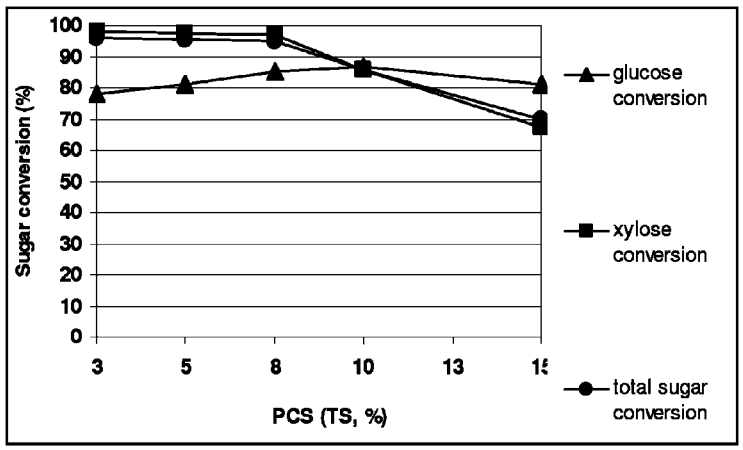

SEQUENCE LISTING

```
<160> NUMBER OF SEQ ID NOS: 14

<210> SEQ ID NO 1
<211> LENGTH: 19
<212> TYPE: DNA
<213> ORGANISM: Artificial Sequence
<220> FEATURE:
<223> OTHER INFORMATION: Primer B-all 27F

<400> SEQUENCE: 1
gagtttgatc ctggctcag                                                    19

<210> SEQ ID NO 2
<211> LENGTH: 21
<212> TYPE: DNA
<213> ORGANISM: Artificial Sequence
<220> FEATURE:
<223> OTHER INFORMATION: Synthetic primer B-all 1492R

<400> SEQUENCE: 2
acggctacct tgttacgact t                                                 21

<210> SEQ ID NO 3
<211> LENGTH: 19
<212> TYPE: DNA
<213> ORGANISM: Artificial Sequence
<220> FEATURE:
<223> OTHER INFORMATION: Synthetic primer B1

<400> SEQUENCE: 3
gagtttgatc ctggctcag                                                    19

<210> SEQ ID NO 4
<211> LENGTH: 21
<212> TYPE: DNA
<213> ORGANISM: Artificial Sequence
<220> FEATURE:
<223> OTHER INFORMATION: Synthetic primer B2

<400> SEQUENCE: 4
acggctacct tgttacgact t                                                 21

<210> SEQ ID NO 5
<211> LENGTH: 26
<212> TYPE: DNA
<213> ORGANISM: Artificial Sequence
<220> FEATURE:
<223> OTHER INFORMATION: Synthetic primer ldhup1F

<400> SEQUENCE: 5
ttccatatct gtaagtcccg ctaaag                                            26

<210> SEQ ID NO 6
<211> LENGTH: 26
<212> TYPE: DNA
<213> ORGANISM: Artificial Sequence
<220> FEATURE:
<223> OTHER INFORMATION: Synthetic primer ldhup2R
```

```
<400> SEQUENCE: 6
attaatacaa tagttttgac aaatcc                                              26

<210> SEQ ID NO 7
<211> LENGTH: 22
<212> TYPE: DNA
<213> ORGANISM: Artificial Sequence
<220> FEATURE:
<223> OTHER INFORMATION: Synthetic primer ldhdown3F

<400> SEQUENCE: 7
atataaaaag tcacagtgtg aa                                                  22

<210> SEQ ID NO 8
<211> LENGTH: 22
<212> TYPE: DNA
<213> ORGANISM: Artificial Sequence
<220> FEATURE:
<223> OTHER INFORMATION: Synthetic primer ldhdown4R

<400> SEQUENCE: 8
cacctatttt gcactttttt tc                                                  22

<210> SEQ ID NO 9
<211> LENGTH: 973
<212> TYPE: DNA
<213> ORGANISM: Artificial Sequence
<220> FEATURE:
<223> OTHER INFORMATION: Synthetic DNA fragment of hydrogenase A
      antisense cassette

<400> SEQUENCE: 9
ctgcagcgcc gcgggatcat cgataagctt gatatcgaat tcctgcagcc ccccccatc         60 ttcatgggaa ttcggagtat atgtcactcc gtggctttat ttttttttatt ttttttactca    120 aaaaaggagg attttttttaa tatacgtcga atatatataa tataagtttg ttgaatcaat     180
aaactattgg ggtggctata taaatgaaaa gaaaattaaa aaacagtgtc ggaatatggg      240
catttggtac ccgacggtat ccgaactata gcaggagaag cattatctat agaatacttt     300
atattttccc cttcaaacct tatttcattt actcctaatt ttttagacaa tgattgaagc     360
tcacagttag tatttctaat acaagtcaaa caacttctat catgatttga agtataagc      420 tcaagattta atttccgcgc ttctcttatt ttagctgtat ttgtatacac tttcatgcca     480
tcaaataccg gataagtgca ggaggtttgt aaatttctaa ctccctctat ttcaactaca     540
catatacggc aagcgccaat ttggttgatt tccttgaggt aacacagtgt ggggatatcg     600
aattcctgca gcccggggga tccactagtt ctagagcggc cgcccacaaa agaattgtaa     660
gaggcccttt tctcttcata cctgtagaaa ggggtctctt aatttctctt tgaaatagaa     720
tatatattcg gttattatat aggtataaat taactacacg cagtctttaa aaaagaagt      780 gatttgtatg gatatatttg aaaaacttga ggtgcttggt gctgccgctc ggtacccgtt      840
gacggcggat atggtacaat gaacatgag acatgcaggg ttttcctgca tttttctttg      900
tgcactcatc aagcgatttt cggtaaagct aggaggaaat gatgaaacga cgaatcagca      960
tcgcaatcga cgg                                                         973

<210> SEQ ID NO 10
<211> LENGTH: 23
<212> TYPE: DNA
<213> ORGANISM: Artificial Sequence
<220> FEATURE:
<223> OTHER INFORMATION: Synthetic primer pforup1F
```

```
<400> SEQUENCE: 10
gaggatttaa gaagggagt tgg                                              23

<210> SEQ ID NO 11
<211> LENGTH: 23
<212> TYPE: DNA
<213> ORGANISM: Artificial Sequence
<220> FEATURE:
<223> OTHER INFORMATION: Synthetic primer pforup2R

<400> SEQUENCE: 11
atttcatctc ccctggata aag                                              23

<210> SEQ ID NO 12
<211> LENGTH: 22
<212> TYPE: DNA
<213> ORGANISM: Artificial Sequence
<220> FEATURE:
<223> OTHER INFORMATION: Synthetic primer pfordown3F

<400> SEQUENCE: 12
cgagagctga ttcccacgaa ga                                              22

<210> SEQ ID NO 13
<211> LENGTH: 24
<212> TYPE: DNA
<213> ORGANISM: Artificial Sequence
<220> FEATURE:
<223> OTHER INFORMATION: Synthetic primer pfordown4R

<400> SEQUENCE: 13
cagactacta caactggatc tagc                                            24

<210> SEQ ID NO 14
<211> LENGTH: 1500
<212> TYPE: DNA
<213> ORGANISM: Thermoanaerobacter mathranii

<400> SEQUENCE: 14
gagtttgatc ctggctcagg acgaacgctg gcggcgtgcc taacacatgc aagtcgagcg     60
gtccggcact caacgtagtt gggtggcgga tagcggcgga cgggtgagta acgcgtgggc    120
aacctaccct taagaccggg atagcacctc gaaagggtg gtaatactgg ataagctcct    180
tatagggcat cctatagggga ggaaagggaa gcgcaagcta ccgcttaagg atgggcccgc    240
gtcccatcag ctagttggta gggtaacggc ctaccaaggc gacgacgggt agccggcctg    300
agagggtggt cggccacact gggactgaga cacggcccag actcctacgg gaggcagcag    360
tggggaatct tgggcaatgg gcggaagcct gacccagcga cgccgcgtgg gggaggaagg    420
ccttcgggtt gtaaaccccg ttagtgtggg aagaagggat gacggtacca cacgaaagcc    480
ccggctaact acgtgccagc agccgcggta agacgtaggg ggcgagcgtt gtccggaatt    540
actgggcgta aagggcgcgt aggcggtcaa tcaagtcagg tgtaaaagac ccggctcaa    600 cccgggggta gcatctgaaa ctgattggct agagggcagg agagggagt ggaattcccg    660 gtgtagcggt gaaatgcgta gatatcggga ggaataccag tggcgaaggc gactctctgg    720 actgccctg acgctgaggc gcgaaagcgt ggggagcgaa caggattaga taccctggta    780
gtccacgctg taaacgatgg gtactaggtg tggggcgcgg aagcgttccg tgccgtagcg    840
aacgcaataa gtacccgcc tggggagtac ggccgcaagg ttgaaactca aggaattga    900 cgggggcccg cacaagcggt ggagcatgtg gtttaattcg aagcaacgcg aagaacctta    960
```

```
ccagggcttg acatgcaggt agtagcgaac cgaaagggga gcgaccttac cgggaggtaa      1020
ggagcctgca caggtggtgc atggttgtcg tcagctcgtg tcgtgagatg ttgggttaag      1080
tcccgcaacg agcgcaaccc ctgcctctag ttgccagcgg gtaagccggg cactctaggg      1140
ggactgccgt ggaggacacg gaggaaggtg gggatgacgt caaatcatca tgccctaaat      1200
gccctgggcc acacacgtgc tacaatggcc ggtacagagg ggagcgaagc cgtgaggcgg      1260
agcgaatccc aaaaagccgg tccaagttcg gattgcaggc tgcaactcgc ctgcatgaag      1320
tcggaatcgc tagtaatcgc ggatcagcat gccgcggtga atacgttccc gggccttgta      1380
cacaccgccc gtcacaccac gagagcctgc gacacccgaa gccggtgacc caaccgggaa      1440
ggagggagcc gtcgaaggtg gggcaggtga ttggggtgaa gtcgtaacaa ggtagccgta      1500
```

THERMOANAEROBACTER MATHRANII STRAIN BG1

CROSS-REFERENCE TO RELATED APPLICATIONS

The present Application is a U.S. national phase of PCT/DK2007/000241 filed on May 22, 2007 ("PCT Application"), which claims priority from Denmark Application No. PA200600703 filed on May 22, 2006, both of which are hereby incorporated by reference in their entirety into the present Application. The PCT application, incorporated by reference herein, includes any amendments entered in the PCT application.

TECHNICAL FIELD

The present invention relates to a novel thermophilic bacterium belonging to the group of *Thermoanaerobacter mathranii*.

BACKGROUND OF THE INVENTION

The industry of producing fermentation products such as ethanol and lactic acid, is facing the challenge of redirecting the production process from fermentation of relatively easily convertible but expensive starchy materials, to the complex but inexpensive lignocellulosic biomass such as wood and residues from agricultural crops, e.g. straw. Unlike starch, which contains homogenous and easily hydrolyzed polymers, lignocellulosic biomass contains cellulose (25-53%), hemicellulose (20-35%), polyphenolic lignin (10-25%) and other extractable components. Typically, the first step in utilization of lignocellulosic biomass is a pre-treatment step, in order to fractionate the components of lignocellulosic material and increase their surface area. The pre-treatment method most often used is acid hydrolysis, where the lignocellulosic material is subjected to an acid such as sulphuric acid whereby the sugar polymers cellulose and hemicellulose are partly or completely hydrolyzed to their constituent sugar monomers. Another type of lignocellulose hydrolysis is steam explosion, a process comprising heating of the lignocellulosic material by steam injection to a temperature of 190-230° C. A third method is wet oxidation wherein the material is treated with oxygen at 150-185° C. The pre-treatments can be followed by enzymatic hydrolysis to complete the release of sugar monomers. This pre-treatment step results in the hydrolysis of cellulose into glucose while hemicellulose is transformed into the pentoses xylose and arabinose and the hexoses glucose, galactose and mannose. Thus, in contrast to starch, the hydrolysis of lignocellulosic biomass results in the release of pentose sugars in addition to hexose sugars. This implies that useful fermenting organisms need to be able to convert both hexose and pentose sugars to a desired fermentation products such as ethanol.

Traditional microorganisms used for e.g. ethanol fermentation, *Saccharaomyces cerevisiae* and *Zymomonas mobilis*, do not metabolize pentoses such as xylose and arabinose, and extensive metabolic engineering is thus necessary to improve performance on lignocellulosic substrates. Gram-positive thermophilic bacteria have unique advantages over the conventional ethanol production strains. The primary advantages are their broad substrate specificities and high natural production of ethanol. Moreover, ethanol fermentation at high temperatures (55-70° C.) has many advantages over mesophilic fermentation. One advantage of thermophilic fermentation is the minimization of the problem of contamination in continuous cultures, since only a few microorganisms are able to grow at such high temperatures in un-detoxified lignocellulose hydrolysate.

Presently, dependent on the pre-treatment method, cellulases and hemicellulases often have to be added to the pre-treated lignocellulosic hydrolysate in order to release sugar-monomers. These enzymes contribute significantly to the production costs of the fermentation products. However, many thermophilic gram-positive strains possess a range of the relevant enzymes and supplementary additions could become less expensive if a thermophilic gram-positive strain is used. Fermentation at high temperature also has the additional advantages of high productivities and substrate conversions and facilitated product recovery.

Lignocellulose hydrolysates contain inhibitors such as furfural, phenols and carboxylic acids, which can potentially inhibit the fermenting organism. Therefore, the organism must also be tolerant to these inhibitors. The inhibitory effect of the hydrolysates can be reduced by applying a detoxification process prior to fermentation. However, the inclusion of this extra process step increases significantly the total cost of the fermentation product and should preferably be avoided. For example, it has been estimated that overliming of willow hydrolysate increases the cost of ethanol production using *Escherichia coli* by 22% (Von Sivers et al., 1994, *Biotechnol. Prog.* 10(5), 555-560). It is therefore preferred that the microorganism is capable of producing fermentation products from undetoxified hemicellulose or holocellulose hydrolysates to make it usable in an industrial lignocellulosic-based fermentation process due to the high cost of detoxification process.

It is also particularly advantageous if the potential microorganism is capable of growing on high concentrations of lignocellulosic hydrolysates, i.e. lignocellulosic hydrolysates with high dry-matter content. This is of particular importance when the microorganism is for alcohol production such as ethanol production, since distillation costs increase with decreasing concentrations of alcohol.

U.S. Pat. No. 6,555,350 describes a *Thermoanaerobacter* strain which is capable of converting pentoses to ethanol. However, this strain has a significant side production of lactate and has only been tested in lignocellulosic hydrolysate having a dry-matter concentration of less than 6% wt/wt.

Larsen et al., 1997 describes a *Thermoanaerobacter mathranii* strain A3 which could only grow in wheat straw hydrolysate with a 6% dry-matter concentration (60 g/l dry weight of wheat straw supplemented with xylose) and is reported not to be able to grow on galactose.

It is therefore one object of the present invention to provide a microorganism which is capable of overcoming the above mentioned obstacles, in particular for the production of ethanol.

SUMMARY OF THE INVENTION

Accordingly, the present invention pertains to a *Thermoanaerobacter mathranii* bacterial strain selected from BG1 (DSMZ Accession number 18280) and mutants thereof. The invention is based on the isolation of the bacterial strain BG1 which is capable of growing and producing fermentation products on very high dry-matter concentrations of lignocellulosic hydrolysates. Furthermore, BG1 has broad substrate specificity, and is capable of utilizing pentoses such as xylose and arabinose and hexoses. The strain further has the advantage of being thermophilic and thus is capable of growing at high temperatures resulting in high productivities and substrate conversion rates, low risk of contamination and facilitated product recovery.

The invention further relates to a method of producing a fermentation product by culturing a strain according to the invention under suitable conditions.

DETAILED DESCRIPTION OF THE INVENTION

As mentioned above, the present invention pertains to a *Thermoanaerobacter mathranii* strain selected from BG1 and mutants thereof.

The invention is based on the isolated bacterial strain BG1 which has been deposited in accordance with the terms of the Budapest Treaty on 17 May 2006 with DSMZ—Deutsche Sammlung von Mikroorganismen and Zellkulturen GmbH, Mascheroder Weg 1b, 38124 Braunschweig, Germany under DSMZ accession number 18280.

As is apparent from the following, the preferred bacteria of the present invention have been deposited. Other bacteria of the present invention can therefore be obtained by mutating the deposited bacteria and selecting derived mutants having enhanced characteristics. Desirable characteristics include an increased range of sugars that can be utilized, increased growth rate, ability to produce higher amounts of fermentation products such as ethanol, etc. Suitable methods for mutating bacteria and selecting desired mutants are described in Functional analysis of Bacterial genes: A practical Manual, edited by W. Schumann, S.D. Ehrlich & N. Ogasawara, 2001.

The base strain BG1 is capable of growing and producing fermentation products on very high dry-matter concentrations of lignocellulosic hydrolysates. In the present context the term "lignocellulosic hydrolysate" is intended to designate a lignocellulosic biomass which has been subjected to a pre-treatment step whereby lignocellulosic material has been at least partially separated into cellulose, hemicellulose and lignin thereby having increased the surface area of the material. The lignocellulosic material may typically be derived from plant material, such as straw, hay, garden refuse, comminuted wood, fruit hulls and seed hulls.

The pre-treatment method most often used is acid hydrolysis, where the lignocellulosic material is subjected to an acid such as sulphuric acid whereby the sugar polymers cellulose and hemicellulose are partly or completely hydrolysed to their constituent sugar monomers. Another type of lignocellulose hydrolysis is steam explosion, a process comprising heating of the lignocellulosic material by steam injection to a temperature of 190-230° C. A third method is wet oxidation wherein the material is treated with oxygen at 150-185° C. The pre-treatments can be followed by enzymatic hydrolysis to complete the release of sugar monomers. This pre-treatment step results in the hydrolysis of cellulose into glucose while hemicellulose is transformed into the pentoses xylose and arabinose and the hexoses glucose, galactose and mannose. The pre-treatment step may in certain embodiments be supplemented with treatment resulting in further hydrolysis of the cellulose and hemicellulose. The purpose of such an additional hydrolysis treatment is to hydrolyse oligosaccharide and possibly polysaccharide species produced during the acid hydrolysis, wet oxidation, or steam explosion of cellulose and/or hemicellulose origin to form fermentable sugars (e.g. glucose, xylose and possibly other monosaccharides). Such further treatments may be either chemical or enzymatic. Chemical hydrolysis is typically achieved by treatment with an acid, such as treatment with aqueous sulphuric acid, at a temperature in the range of about 100-150° C. Enzymatic hydrolysis is typically performed by treatment with one or more appropriate carbohydrase enzymes such as cellulases, glucosidases and hemicellulases including xylanases.

It was surprisingly found that the bacterial strain according to invention is capable of growing in a medium comprising a hydrolysed lignocellulosic biomass material having a dry-matter content (or as also used herein "total solids", TS) of at least 10% wt/wt, such as at least 15% wt/wt, including at least 20% wt/wt, and even as high as at least 25% wt/wt. As mentioned previously, this has the great advantage that it may not be necessary to dilute the hydrolysate before the fermentation process, and thereby it is possible to obtain higher concentrations of fermentation products such as ethanol, and thereby the costs for subsequently recovering the fermentation products may be decreased. For example the distillation costs for ethanol will increase with decreasing concentrations of alcohol.

The bacterial strain according to the invention is an anaerobic thermophilic bacterium, and it is capable of growing at high temperatures even at or above 70° C. The fact that the strain is capable of operating at this high temperature is of high importance in the conversion of the lignocellulosic material into fermentation products. The conversion rate of carbohydrates into e.g. ethanol is much faster when conducted at high temperatures. For example, ethanol productivity in a thermophilic *Bacillus* is up to ten-fold faster than a conventional yeast fermentation process which operates at 30° C. Consequently, a smaller production plant is required for a given volumetric productivity, thereby reducing plant construction costs. As also mentioned previously, at high temperature, there is a reduced risk of contamination from other microorganisms, resulting in less downtime, increased plant productivity and a lower energy requirement for feedstock sterilization. The high operation temperature may also facilitate the subsequent recovery of the resulting fermentation products.

Numerous fermentation products are valuable commodities which are utilized in various technological areas, including the food industry and the chemical industry. Presently, the increasing global energy requirements have resulted in increasing focus on alternatives to fossil fuels as energy sources, and ethanol derived from plant materials (bioethanol) has received particular attention as a potential replacement for or supplement to petroleum-derived liquid hydrocarbon products.

Lactic acid, which is another fermentation product, is extensively used in the cosmetics industry as an anti-aging chemical, and the food industry use lactic acid in a variety of food stuffs to act as an acidity regulator. Recently, lactic acid has also attracted much attention for its potential use in biodegradable polyesters.

The strain according to invention has the potential to be capable of producing a number of different fermentation products, including acids, alcohols, ketones and hydrogen. In one embodiment, the alcohol is selected from ethanol, butanol, propanol, methanol, propanediol and butanediol. In a further embodiment the acid is lactic acid, proprionate, acetate, succinate, butyrate or formate and the ketone is acetone.

As mentioned above, BG1 is a wild type strain isolated from an Icelandic hot-spring, and it has several highly advantageous characteristics needed for the conversion of lignocellulosic biomass material. Thus, this base strain possesses all the genetic machinery for the conversion of both pentose and hexose sugars to various fermentation products such as lactic acid and ethanol.

As will be apparent from the below examples, the examination of the complete 16S rDNA sequence (SEQ ID NO:14) showed that strain BG1 is closely related to *Thermoanaerobacter mathranii* strain A3 (Larsen et al., 1997). This places BG1 in cluster V of the Clostridia. Although the strains are closely related, they are very different when it comes to tolerance to hemicellulosic hydrolysates. A3 could only grow in up to 40% wheat straw hydrolysate (of 60 g/l dry weight of wheat straw supplemented with xylose, i.e. a dry-matter concentration of 6% wt/wt) while BG1 can grow and produce ethanol from undiluted hydrolysate at high dry-matter concentrations (up to at least 25%) with no addition of sugar or enzymes. Furthermore, strain A3 is reported not to be able to grow on galactose (Larsen et al., 1997), whereas BG1 grows nicely and produces primarily ethanol with galactose as the sole carbon source. Thus, the strain according to the invention is capable of growing on galactose as the sole carbon source.

As shown in the accompanying examples the first hours of BG1 growth at pH=7 and 70° C. in xylose minimal medium, ethanol and acetate are produced in equimolar amounts. When the culture then enters late exponential phase, the specific ethanol production exceeds that of acetate significantly. The pH after fermentation was unchanged, and it is therefore not expect the effect to be caused by pH. Likewise, it was shown that by replacing the headspace $N_2/CO_2$ with pure hydrogen or adding acetate had no effect on the fermentation, and the mechanisms behind the shift to ethanol formation in late exponential phase are therefore still elusive.

The examples also illustrate that the pH of the medium has a strong effect on the product profile of BG1. Above pH 6.5, the production of ethanol was dominant, and almost no lactate was produced. Below pH 6.0, lactate production increased at the expense of ethanol, and at pH 5.0, no growth was observed. The same effect of pH on lactate production has been observed for the closely related thermophilic bacterium *Thermoanaerobacter wiegelii*. Crude cell extracts were found to contain a fructose-1,6-diphosphate (FDP) activated lactate dehydrogenase (LDH). The affinity of FDP was dependent on extracellular pH. Maximal activation was observed at pH 6.2, and no activation was observed at pH 8.2 (Cook, 2000). Since this effect is common in *Thermoanaerobacter* species, it is also likely to be the cause in BG1 (Lamed and Zeikus, 1980; Carreira et al., 1982; Bryant, 1991).

The following examples also illustrate the effect of addition of ethanol on the growth rate and metabolite distribution of BG1. Low ethanol tolerance is a major obstacle for the commercial exploitation of thermophilic bacteria and selection for ethanol resistant strains is therefore of great importance. However, an ethanol resistant mutant of *Clostridium thermohydrosulfuricum,* 39EA, could grow at ethanol concentrations up to 8% (w/v) at 45° C., and up to 3.3% (w/v) at 68° C. (Lovitt et al., 1984), and a mutant strain of *Thermoanaerobacter ethanolicus*, 39E-H8, displayed an ethanol tolerance of 8% at 60° C. (Burdette et al., 2002). BG1 is very tolerant to ethanol at 70° C., when compared to other thermophilic anaerobic strains (Herrero and Gomez, 1980; Larsen et al., 1997; Lovitt et al., 1988; Wiegel and Ljungdahl, 1981; Rani et al., 1996). At 2.8% of exogenous ethanol, the growth rate was still 27% of the rate without ethanol added, in an unadapted culture.

*Thermoanaerobacter ethanolicus* E39 has been reported to consume exogenously added ethanol using the primary alcohol dehydrogenase (Burdette et al., 2002). This is the case even in the ethanol tolerant mutant E39-H8, which has no (or decreased) primary alcohol dehydrogenase activity. In contrast, BG1 was found to produce ethanol even at high concentrations of exogenous ethanol. The lactate production was found to increase in BG1 when ethanol was added. Ethanol production at high ethanol concentrations is pivotal for ethanol producing microorganisms.

As opposed to starchy or cellulosic substrates, which are almost exclusively broken down to glucose, lignocellulosic biomass contains several different sugar monomers, including both hexoses and pentoses. If these are to be converted into a fermentation product such as ethanol in a continuous process, it is necessary for all the sugars to be taken up and metabolized simultaneously. Co-fermentation has proven to be problematic in many of the traditional ethanol producing microorganisms. *Saccharomyces cerevisiae* and *Zymomonas* MOMS have been successfully engineered for cofermentation of glucose and xylose, but cofermentations with arabinose seem to be more problematic (Dien et al., 2000; Lawford and Rousseau, 2002; Ho et al., 1998). In gram positive bacteria in which carbon metabolism was studied at the molecular level, glucose was shown to inhibit transcription of the xylAB operon encoding enzymes responsible for the initial metabolism of xylose, by catabolite repression (Hueck and Hillen, 1995). In contrast, transcription of the xylAB operon of *Thermoanaerobacter ethanolicus* is not repressed by glucose, and a simultaneous degradation of glucose and xylose is seen (Erbeznik et al., 1998). As shown in the Examples, BG1 degraded the sugar mixture of glucose, xylose, arabinose and galactose simultaneously as well as the mixture of glucose, xylose, galactose and mannose.

The hydrolysis of lignocellulosic biomass results in release of microbial inhibitors (Klinke et al., 2004), and washing of the hydrolysate might therefore increase BG1 ethanol productivity. However, in the experiments shown in the Examples, washing significantly decreased the ethanol productivity of BG1. This effect is likely to be caused by washing out of readily fermentable pentosans, thereby lowering the initial sugar concentration. In a similar study on pretreated aspen wood, it was shown that washing efficiently removed inhibitors, but also resulted in a drastic 75% loss of available pentosans (Saddler and Chan, 1984). The presence of inhibitors in the hydrolysate does not seem to be a major obstacle for BG1 fermentations, and BG1 seems to have a great advantage over traditional ethanol producing microorganisms in concentrated non-detoxified lignocellulosic hydrolysates.

It is demonstrated in the following examples, that the base strain BG1 in advantageous embodiments may be modified in order to obtain mutants or derivatives of BG1, with improved characteristics. Thus, in one embodiment there is provided a bacterial strain according to the invention which is a variant or mutant of BG1 wherein one or more genes have been inserted, deleted or substantially inactivated. Genes may be inserted, deleted or substantially inactivated using suitable gene manipulation tools and genetic engineering procedures which are well known in the art, e.g. gene cloning systems, homologous recombination and techniques described in Sambrook & Russell "Molecular Cloning: A Laboratory Manual" (Third Edition, 2001), Cold Spring Harbor Laboratory Press.

In particular, it has surprisingly been found by the present inventors, that the ethanol producing capability of BG1 may be significantly increased by inactivating the gene encoding lactate dehydrogenase (LDH) (EC 1.1.1.27). Thus it was found, that the ethanol production, when grown on glucose, was increased from about 51-56% of the theoretical maximum yield in the wild type BG1 to about 84-91% in the lactate dehydrogenase deficient strain BG1L1.

Therefore, it is contemplated that the strain in accordance with the invention may be a modified version of BG1 wherein the gene encoding lactate dehydrogenase (LDH) (EC 1.1.1.27) has been inactivated by the deletion of said gene, or wherein the gene has been substantially inactivated by the mutation, deletion or insertion of one or more amino acids in gene.

In one embodiment there is provided a lactate dehydrogenase deficient mutant strain BG1L1 which has been deposited in accordance with the terms of the Budapest Treaty on 17 May 2006 with DSMZ—Deutsche Sammlung von Mikroorganismen and Zellkulturen GmbH, Mascheroder Weg 1b, 38124 Braunschweig, Germany under DSMZ accession number 18283.

As mentioned above, lactic acid (or lactate) is a widely used e.g. in the food industry and is therefore a valuable fermentation product. It was found by the present inventors, that the wild type strain BG1 can be modified to produce increased amounts of lactate as compared to the wild type by inactivating the gene encoding pyruvate ferredoxin oxidoreductase (EC 1.2.7.1). Thus, it was found that the metabolism of wild type BG1 could be completely shifted from the production of ethanol to the production of lactate. Hence, it is one object of the invention to provide a strain derived from BG1 wherein a gene encoding pyruvate ferredoxin oxidoreductase (EC 1.2.7.1) has been down-regulated or substantially inactivated, e.g. inactivated by the mutation, deletion or insertion of one or more amino acids in the gene. More specifically, there is provided a derivative of BG1 having increased lactate producing characteristics which is designated BG1PF1 and has been deposited in accordance with the terms of the Budapest Treaty on 17 May 2006 with DSMZ—Deutsche Samnnlung von Mikroorganismen und Zellkulturen GmbH, Mascheroder Weg 1b, 38124 Braunschweig, Germany under DSMZ accession number 18282.

Hydrogen is widely used in the petroleum and chemical industries, i.a. for the processing of fossil fuels, for hydroalkylation, hydrodesulfurization and hydrocracking, and it is used for the hydrogenation of fats and oils (found in items such as margarine), and in the production of methanol. Additionally, hydrogen can be used as an energy source, and can be burned in e.g. combustion engines.

Acetic acid is a valuable product which is widely used in industry, mainly for the production of vinyl acetate monomer, ester production, vinegar, and for use as a solvent. The global demand of acetic acid is around 6.5 million tonnes per year.

The present inventors have constructed an improved BG1 mutant strain, which is capable of producing both more hydrogen and acetic acid in the form of acetate than the wild type strain BG1. This was performed by down-regulation of the HydABCD gene encoding hydrogenase of BG1.

Thus in accordance with the invention, there is provided a mutant strain or derivative of BG1, wherein a gene encoding a hydrogenase or a hydrogenase subunit has been down-regulated or substantially inactivated. The inactivation of the gene may be performed by mutation, deletion or insertion of one or more amino acids in the gene. More specifically, the gene encoding hydrogenase or a hydrogenase subunit may be selected from [Fe]-hydrogenases and [NiFe]-hydrogenases (EC 1.6.5.3, EC 1.12.7.2, EC 1.12.99.6) such as NuoE, NuoF, NuoG, EchB, EchC, EchD, EchE and EchF.

Accordingly, in one embodiment there is provided a strain according to the invention having improved hydrogen and acetic acid production capabilities which is designated BG1H1. BG1H1 has been deposited in accordance with the terms of the Budapest Treaty on 17 May 2006 with DSMZ—Deutsche Sammlung von Mikroorganismen und Zellkulturen GmbH, Mascheroder Weg 1b, 38124 Braunschweig, Germany under DSMZ accession number 18281.

It is further contemplated, that in certain embodiments, it may be useful to down-regulate or substantially inactivate a gene encoding an acetate kinase (EC 2.7.2.1) and/or phosphate acetyltransferase (EC 2.3.1.8) in BG1 or mutants thereof. The inactivation may be performed by mutation, deletion or insertion of one or more amino acids in said genes.

As mentioned above, BG1 posses the genetic machinery to enable it to convert both hexose sugars and pentose sugars to a range of desired fermentation products, including ethanol.

However, it may for certain embodiments be desired to insert one or more additional genes into the strain according to the invention. Thus, in order to improve the yield of the specific fermentation product, it may be beneficial to insert one or more genes encoding a polysaccharase into the strain according to the invention. Hence, in specific embodiments there is provided a strain according to the invention wherein one or more genes encoding a polysaccharase which is selected from cellulases (such as EC 3.2.1.4); beta-glucanases, including glucan-1,3 beta-glucosidases (exo-1,3 beta-glucanases, such as EC 3.2.1.58), 1,4-beta-cellobiohydrolase (such as EC 3.2.1.91) and endo-1,3(4)-beta-glucanases (such as EC 3.2.1.6); xylanases, including endo-1,4-beta-xylanases (such as EC 3.2.1.8) and xylan 1,4-beta-xylosidase (such as EC 3.2.1.37); pectinases (such as EC 3.2.1.15); alpha-glucuronidase, alpha-L-arabinofuranosidase (such as EC 3.2.1.55), acetylesterase (such as EC 3.1.1.-), acetylxylanesterase (such as EC 3.1.1.72), alpha amylase (such as EC 3.2.1.1), beta-amylase (such as EC 3.2.1.2), glucoamylase (such as EC 3.2.1.3), pullulanase (such as EC 3.2.1.41), beta-glucanase (such as EC 3.2.1.73), hemicellulase, arabinosidase, mannanases including mannan endo-1,4-beta-mannosidase (such as EC 3.2.1.78) and mannan endo-1,6-alpha-mannosidase (such as EC 3.2.1.101), pectin hydrolase, polygalacturonase (such as EC 3.2.1.15), exopolygalacturonase (such as EC 3.2.1.67) and pectate lyase (such as EC 4.2.2.10).

Depending on the desired fermentation product, it is contemplated that in certain embodiments it is useful to insert heterologous genes encoding a pyruvate decarboxylase (such as EC 4.1.1.1) or to insert a heterologous gene encoding an alcohol dehydrogenase (such as EC 1.1.1.1, EC 1.1.1.2, EC 1.1.1.71, or EC 1.1.99.8) or to up-regulate an already existing gene encoding alcohol dehydrogenase.

In accordance with the invention a method of producing a fermentation product comprising culturing a strain according to the invention under suitable conditions is also provided.

The strain according to the invention is a strict anaerobic microorganism, and hence it is preferred that the fermentation product is produced by a fermentation process performed under strict anaerobic conditions. Additionally, the strain according to invention is a thermophilic microorganism, and therefore the process may perform optimally when it is operated at temperature in the range of about 40-95° C., such as the range of about 50-90° C., including the range of about 60-85° C., such as the range of about 65-75° C.

For the production of certain fermentation products, it may be useful to select a specific fermentation process, such as batch fermentation process, including a fed batch process or a continuous fermentation process.

In accordance with the invention, the method is useful for the production of a wide range of fermentation products including acids, alcohols, ketones and hydrogen. Thus fermentation products such as ethanol, butanol, propanol, methanol, propanediol, butanediol, lactic acid, propionate, acetate, succinate, butyrate, formate and acetone may be produced in accordance with the invention.

The invention will now be further described in the following non-limiting examples and figures.

SHORT DESCRIPTION OF THE FIGURES

FIG. 1. Phylogenetic tree based on 16S rDNA sequence analysis showing the position of strain BG1 among related thermophilic Clostridia. T. is a *Thermoanaerobacter* species, Tm. is a *Thermoanaerobacterium*. The bar shows 2% nucleotide substitutions.

Figure 2:
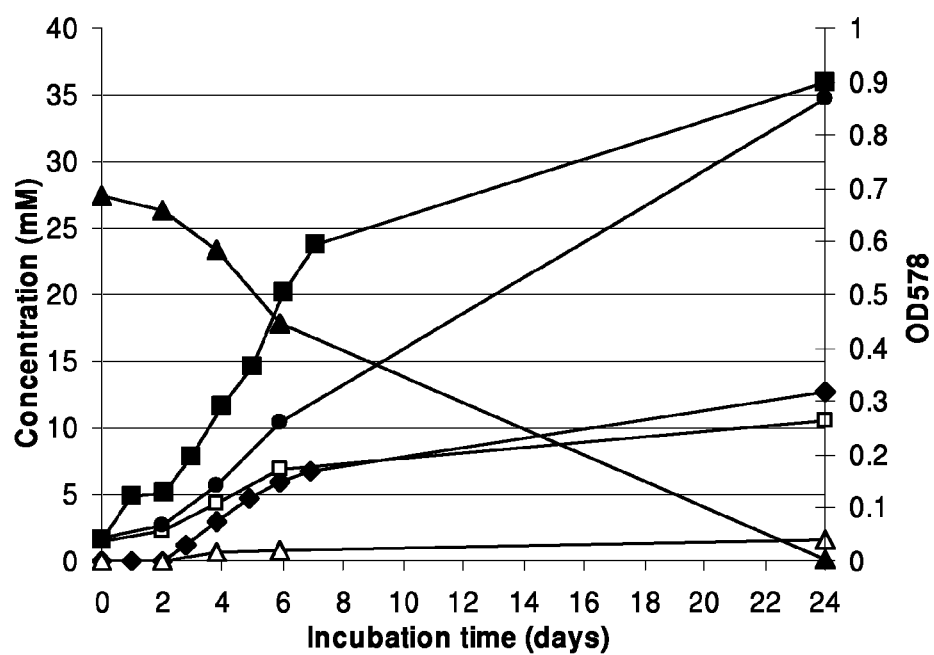

FIG. 2: Product distribution from a 24 hour batch fermentation of BG1. ▲: xylose (mM), Δ: lactate (mM), □: acetate (mM), ●: ethanol (mM), ♦: hydrogen (mM), ■: cell density (OD578).

Figure 3:
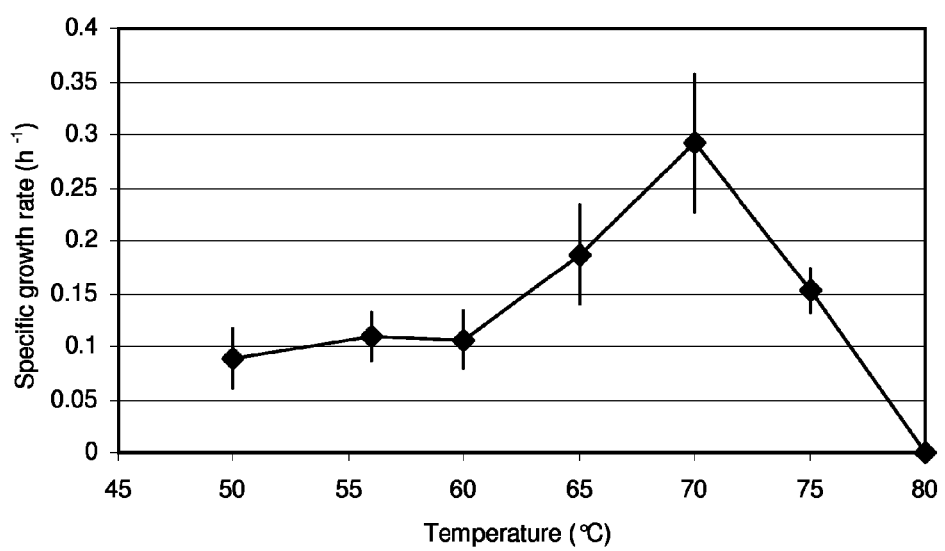

FIG. 3. Effect of temperature on the specific growth rate of strain BG1 grown anaerobically in batch with 5 g/l xylose. Standard deviations from 3 independent measurements are shown with bars.

Figure 4:
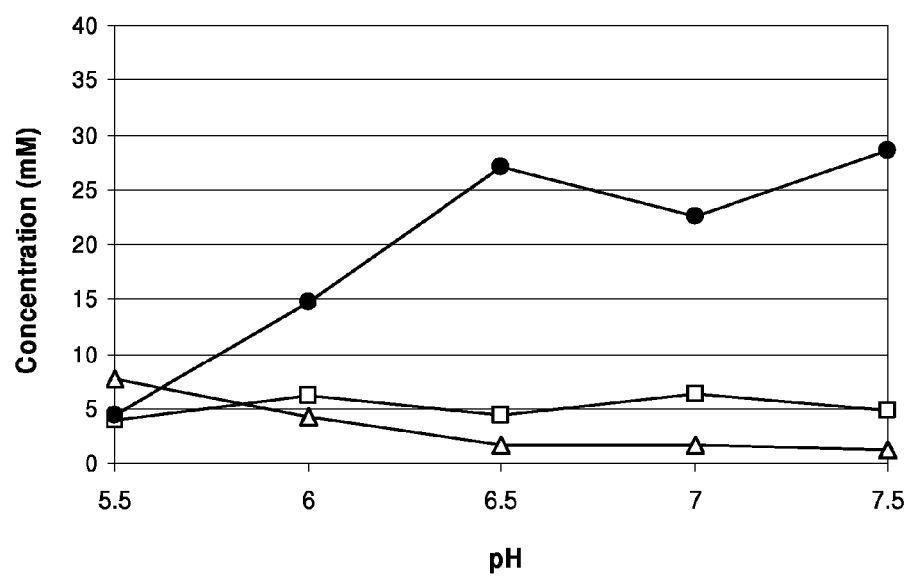

FIG. 4. Product formation from BG1 batch fermentations at different pH. Δ: lactate (mM), □: acetate (mM), ●: ethanol (mM).

Figure 5:
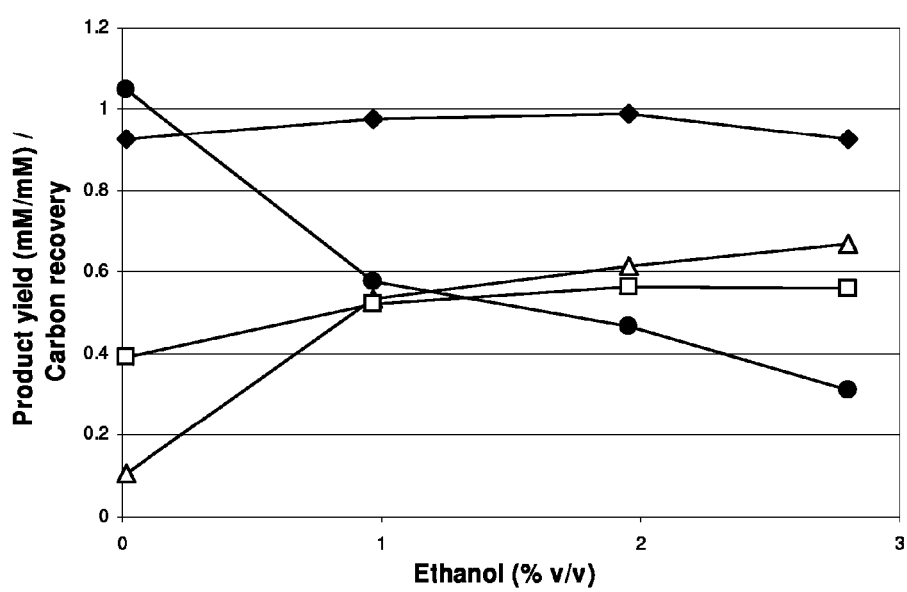

FIG. 5. Batch fermentations with strain BG1 grown on BA medium with 5 g/l xylose and varying concentrations of ethanol added to the medium. The product yield in mM product per g xylose consumed is shown as a function of the initial ethanol concentration in the medium. □: acetate, Δ: lactate, ●: ethanol, ♦: carbon recovery.

Figure 6:
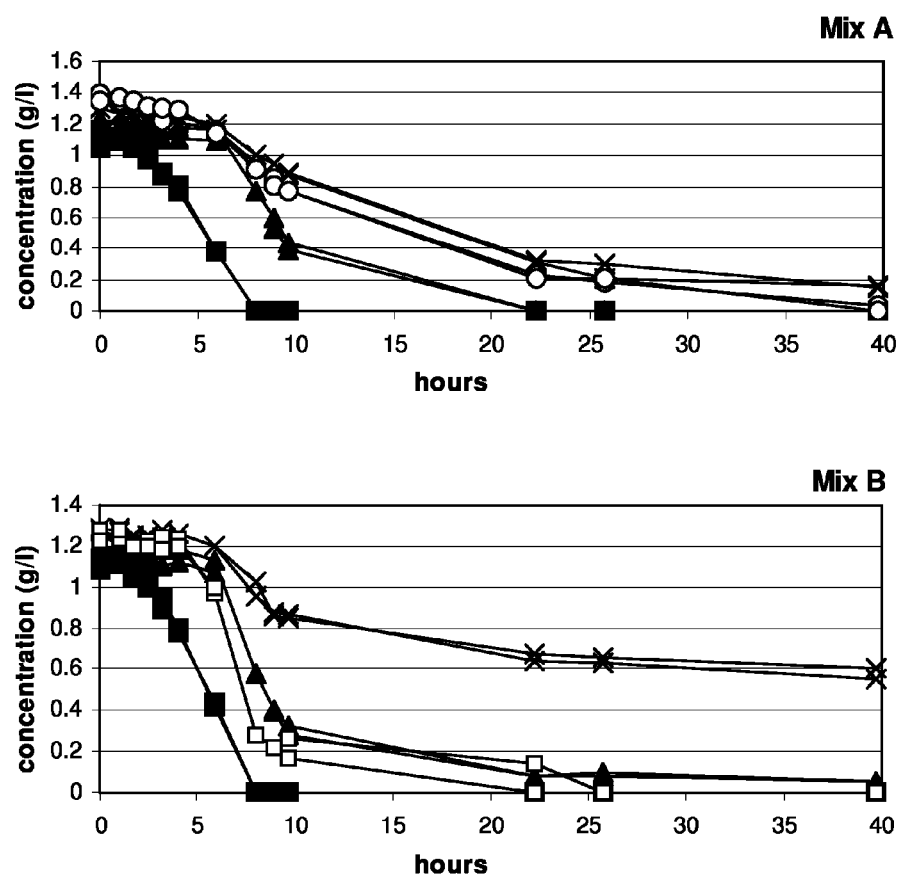

FIG. 6. BG1 sugar consumption in batch fermentation with mixed sugars as carbon source. The sugar concentration of two different sugar mixture experiments (each in duplicate) is shown as a function of time after inoculation with strain BG1. ■: glucose, ▲: xylose, ○: arabinose, x: galactose, □: mannose FIG. 7. BG1 (open symbols) and BG1L1 (closed symbols) grown in batch at varying concentrations of glucose. A: Ethanol (squares), lactate (circles) and acetate (triangles) as a function of ethanol concentration. B: Carbon recoveries (last row) at the respective glucose concentrations (upper row) of the experiments shown in A.

Figure 8:
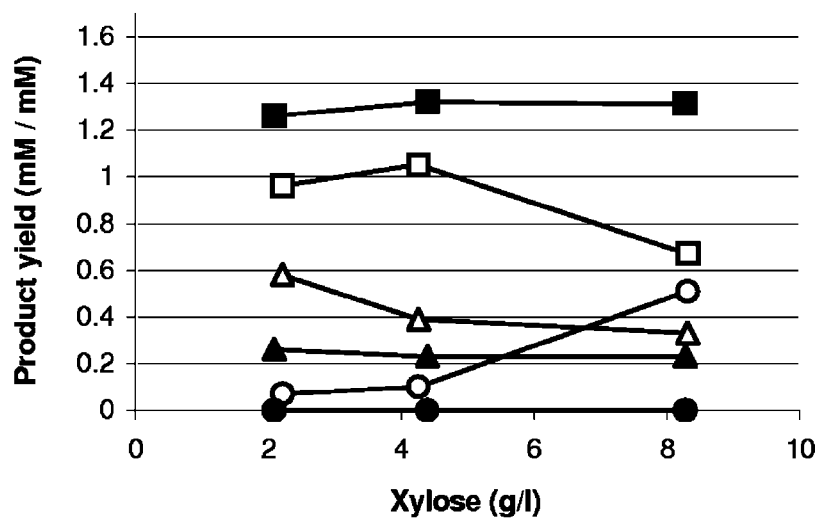

FIG. 8. BG1 (open symbols) and BG1L1 (closed symbols) grown in batch at varying concentrations of xylose. A: Ethanol (squares), lactate (circles) and acetate (triangles) as a function of ethanol concentration. B: Carbon recoveries (last row) at the respective glucose concentrations (upper row) of the experiments shown in A FIG. 9. BG1 (open symbols) and BG1L1 (closed symbols) grown in batch at varying concentrations of exogenously added ethanol. A: Ethanol (squares), lactate (circles) and acetate (triangles) as a function of ethanol concentration. B: Carbon recoveries (last row) at the respective glucose concentrations (upper row) of the experiments shown in A.

FIG. 10. Abbreviations in Table: HRT: hydraulic retention times, Glu: glucose, Xyl: xylose, Ace: acetate, CGlu: consumed glucose, CXyl: consumed xylose, CS: total sugar consumed, $Y_{Ace/TS}$: acetate yield (g/g initial sugars, $Y_{EtOH/TS}$: ethanol yield (g/g initial sugars), $Y_{EtOH/TS}$: ethanol yield of initial sugars corrected for ethanol evaporation, $Q_{EtOH}$: volumetric ethanol productivity, CR: carbon recovery.

Figure 11:
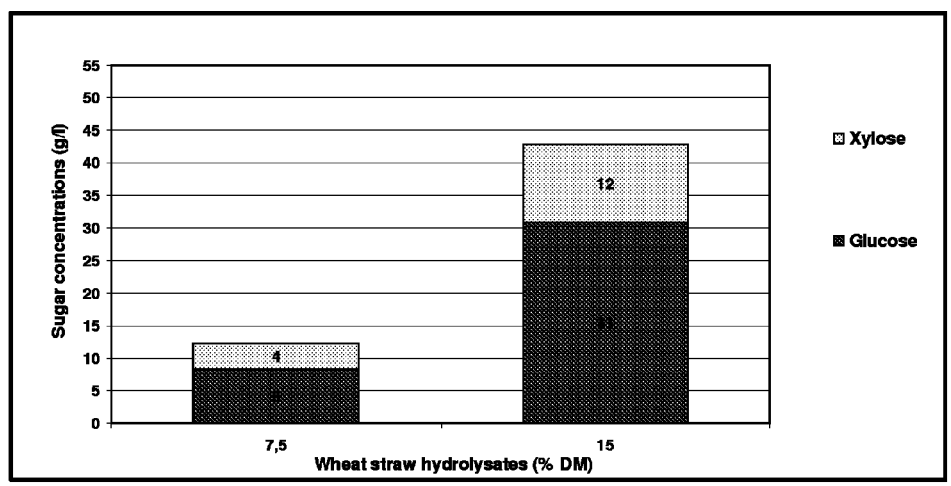

FIG. 11. Influent sugar concentrations of various wheat straw hydrolysate suspensions at 7.5% and 15% DM, indicating the glucose and xylose concentrations at the respective DM concentrations. Undiluted wheat straw hydrolysate (23% DM-Dry Matter; 77 g/l soluble sugars; 57 g/l glucose and 20 g/l xylose).

Figure 12:
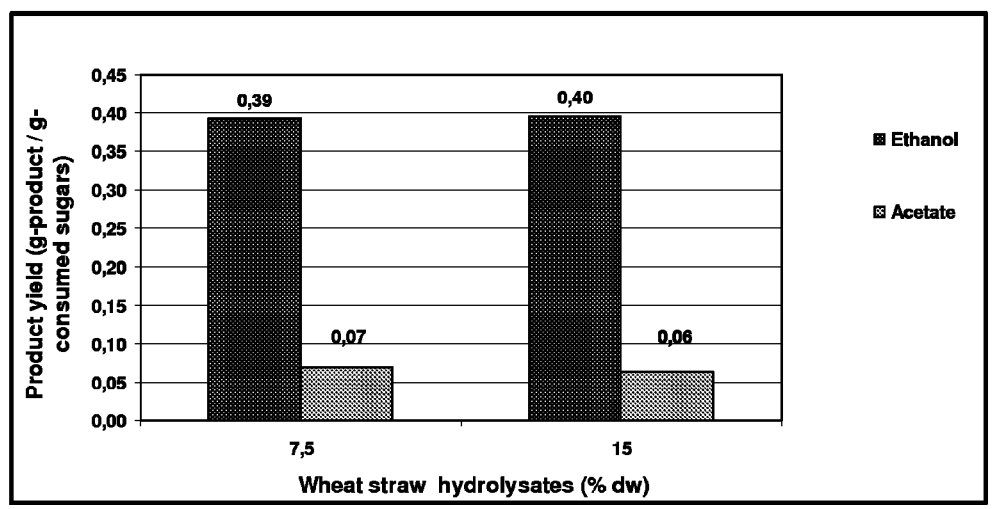

FIG. 12. Product yields obtained with a BG1L1 in a FBR—reactor at 70° C. from various wheat straw hydrolysate suspensions.

FIG. 13. Influent sugar concentrations (A) and sugar conversions (B) for various acid hydrolyzed corn stover hydrolysate suspensions from a continuous fluidized bed reactor with immobilized thermophilic anaerobic bacterium BG1L1 at 70° C. (PCS=Corn stover hydrolysate).

Figure 14:
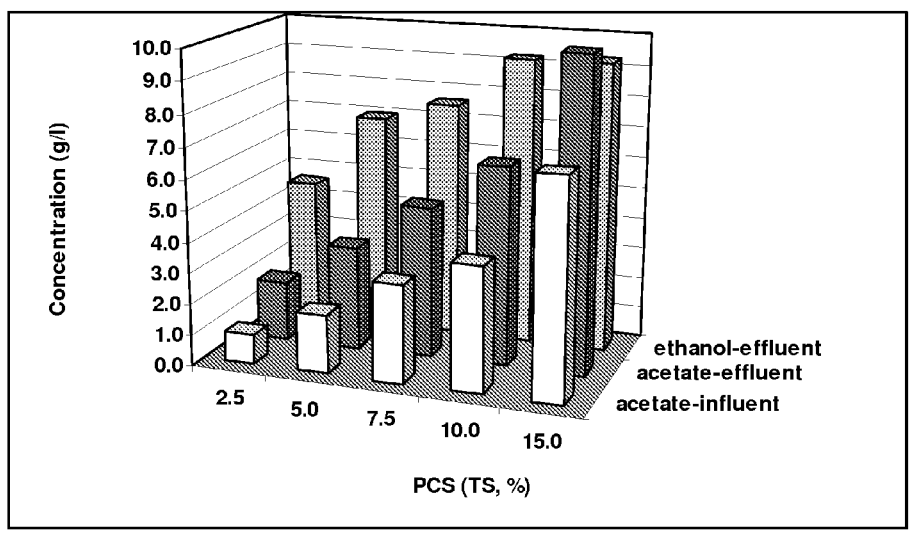

FIG. 14. Effluent product concentrations (acetate and ethanol) and influent acetate concentration for various acid hydrolyzed corn stover hydrolysate suspensions from continuous fluidized bed reactor with immobilized thermophilic anaerobic bacterium BG1L1 at 70° C.

Figure 15:
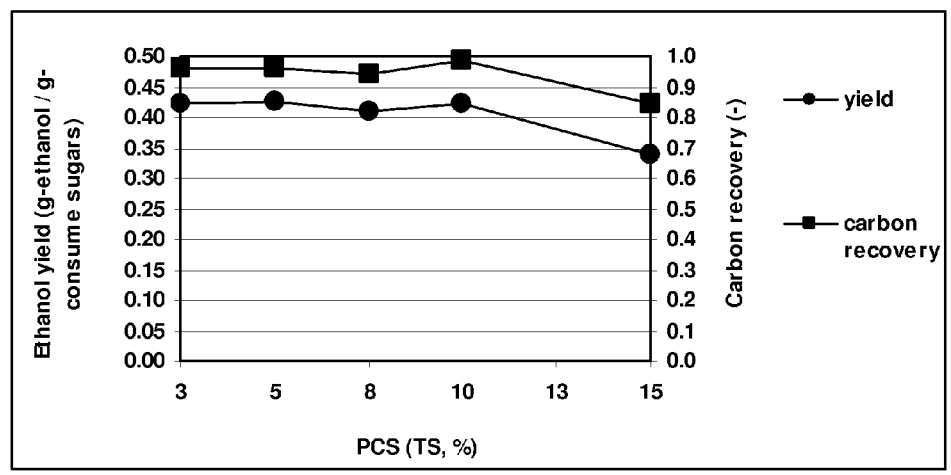

FIG. 15. Ethanol yield and carbon recovery for various acid hydrolyzed corn stover hydrolysate suspensions from continuous fluidized bed reactor with immobilized thermophilic anaerobic bacterium BG1L1 at 70° C.

Figure 16:
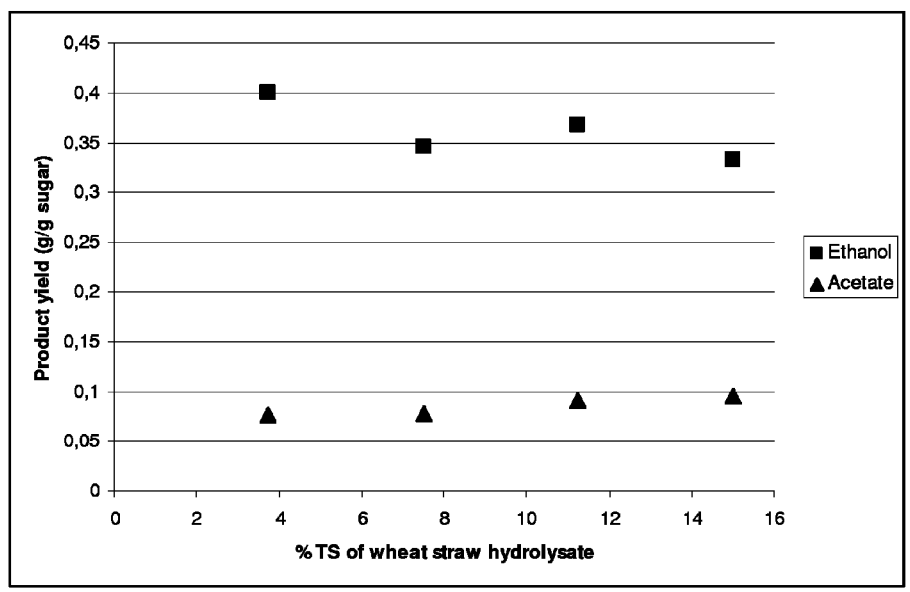

FIG. 16. Ethanol and acetate yield for various wet exploded wheat straw hydrolysate suspensions from a continuous fluidized bed reactor with the immobilized thermophilic anaerobic bacterium BG1L1 at 70° C.

Figure 17:

FIG. 17. Construct used for deletion of a 7762 bp region, containing pyruvate ferredoxin oxidoreductase subunit encoding genes, from the chromosome of BG1. up: a region upstream of the BG11 pyruvate ferredoxin oxidoreductase. down: a region downstream of the BG1 pyruvate ferredoxin oxidoreductase. HTK: a gene encoding a highly thermostable kanamycin resistance cassette.

Figure 18:
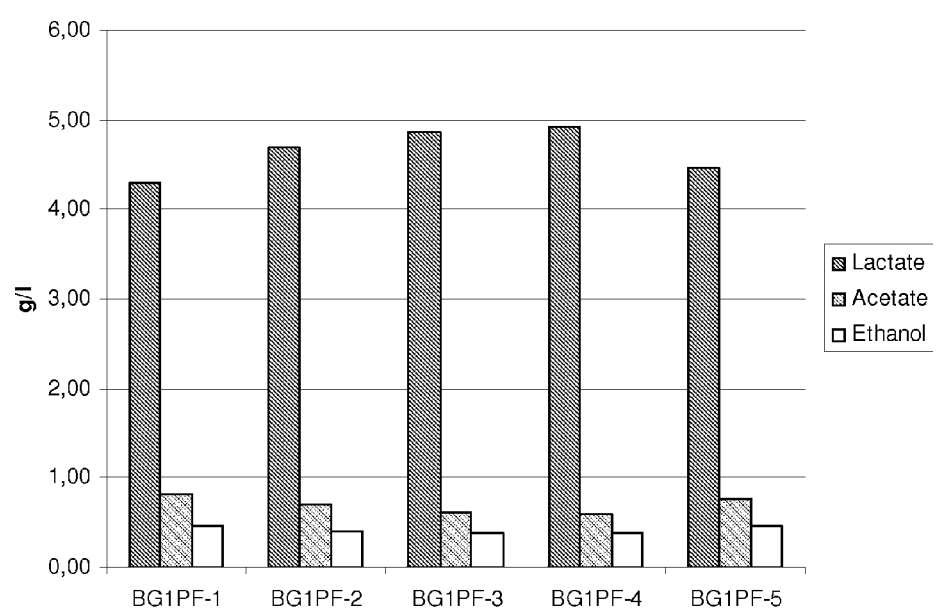

FIG. 18. End-product distribution after batch fermentation at 70° C. with five independent clones of BG1PF.

Figure 19:
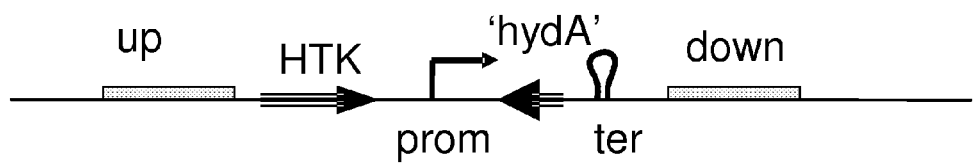

FIG. 19. Construct used for introduction of anti-sense cassettes into the chromosome of BG1. up: a region upstream of the BG1 lactate dehydrogenase. down: a region downstream of the lactate dehydrogenase gene. HTK: a gene encoding a highly thermostable kanamycin resistance cassette. prom: promoter, ter: terminator. a 335 bp fragment from hydA was cloned in the anti-sense direction into a cloning site between the promoter and terminator.

Figure 20:
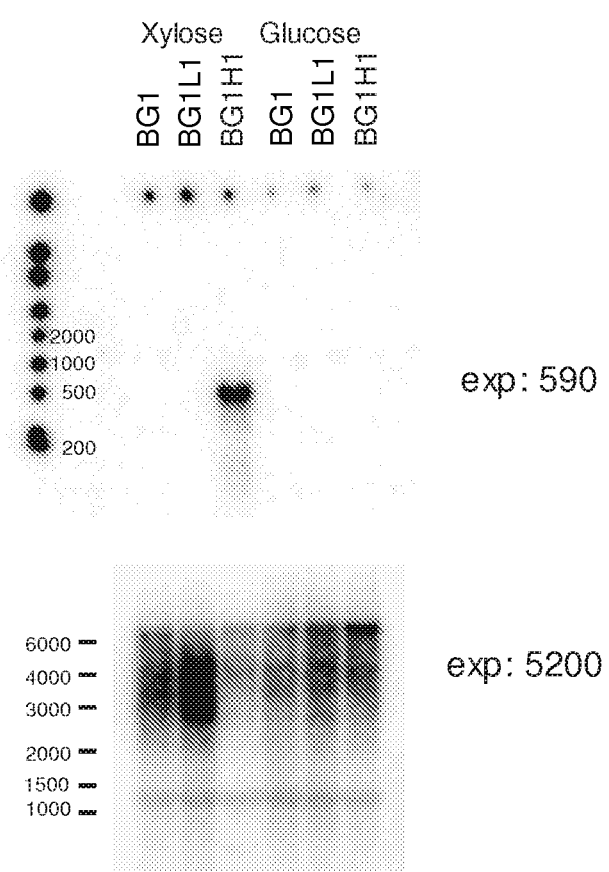

FIG. 20. Northern blot analysis of total RNA isolated from BG1, BG1L1 and BG1H1 grown on glucose or xylose. The RNA was isolated from exponentially growing cells. Upper panel: a probe directed towards the hydA antisense was used. Lower panel: a probe directed towards the hydA part of the hyd mRNA. RNA size marker bands are shown to the right.

Figure 21:
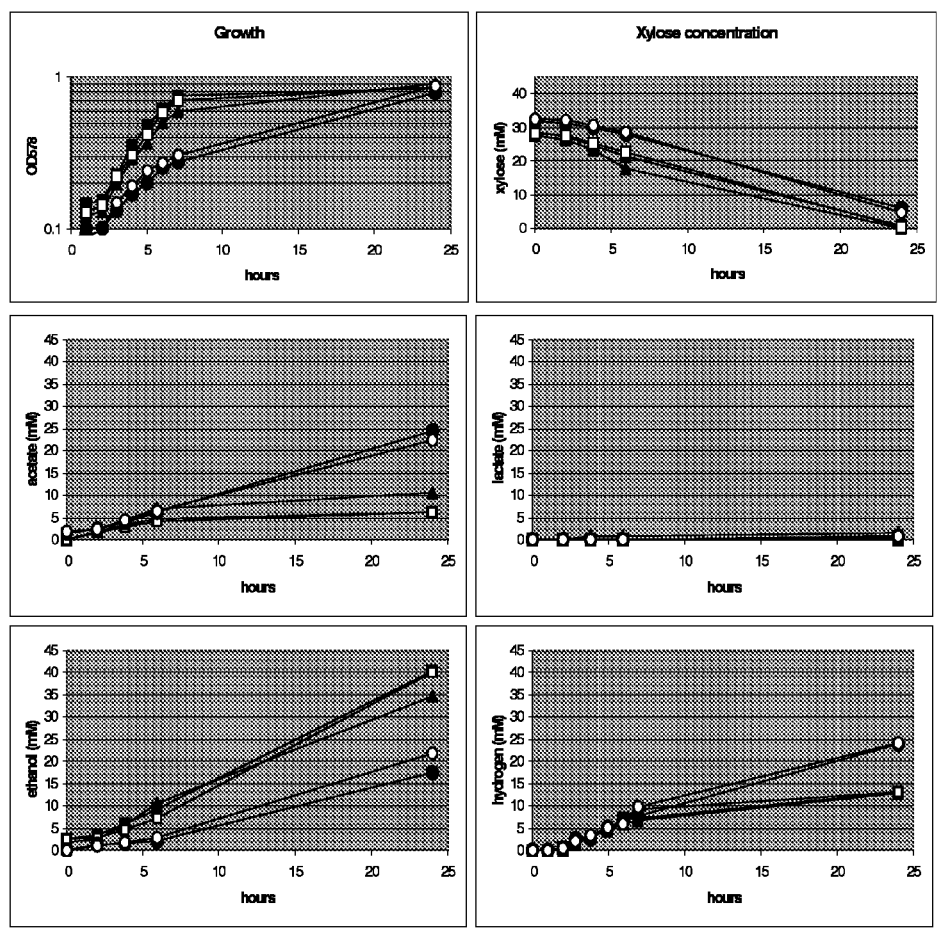

FIG. 21. Growth, xylose consumption, acetate, lactate, ethanol and hydrogen production of BG1 (open and closed squares), BG1L1 (triangles) and BG1H1 (open and closed circles), grown in batch.

The term "Figure" may be abbreviated herein as "FIG." and "Figures" as "FIGS".

EXAMPLES

Materials and Methods

The following materials and methods were applied in the below Examples:

Strains and Growth Conditions

Strain BG1 was isolated anaerobically from an Icelandic hot-spring at 70° C. All strains were cultured at 70° C. anaerobically in minimal medium (BA) with 2 g/l yeast extract as in (Larsen et al., 1997) unless otherwise stated. For solid medium, roll tubes (Hungate RE, 1969, In: Methods in Microbiology, Norris, J. R. and D. W. Ribbons (Eds). Academic Press, Inc. New York, pp: 117-132; Bryant MP, 1972). American Journal of Clinical Nutrition 25, 1324-1328 containing BA medium with 11 g/l phytagel and additional 3.8 g/l $MgCl_2.6H_2O$ was used. For cloning purposes, *Escherichia coli* Top10 (Invitrogen, USA) was used. Top10 was routinely cultivated at 37° C. in Luria-Bertani medium (Ausubel, F. M. et al., 1997). Current protocols in Molecular Biology, John Wiley & Sons, Inc. supplemented with 100 µg/ml ampicillin and 25 µg/ml kanamycin when needed.

Continuous Reactors

Fermentation medium used for continuous cultivation was prepared and supplemented with the same minerals, trace metals, and yeast extract as described above. The initial pH of the medium was adjusted to 7.4-7.7 and it was autoclaved at 120° C. for 30 min. To insure anaerobic conditions, medium was flushed for 45 minutes with a mixture of N2/$CO_2$ (4:1), and finally $Na_2S$ was injected into the bottle to give a final concentration of 0.25 g/l.

The reactor was a water-jacketed glass column with 4.2 cm inner diameter and 20 cm height. The working volume of the reactor was 200 ml. The influent entered from the bottom of the reactor and the feeding was controlled by a peristaltic pump (Model 503S-10rpm, Watson Marlow, Falmouth, UK). Recirculation flow was achieved by using an identical peristaltic pump (Model 503-50 rpm, Watson Marlow, Falmouth, UK), with a degree of recirculation to ensure up-flow velocities in the reactor of 1 m/h. The pH was maintained at 7.0 bp addition of NaOH (1-2M), unless otherwise stated. The reactor was loaded with 75 ml carrier material and finally the entire reactor system, including tubing and recirculation reservoir, was autoclaved at 120° C. for 30 min. Liquid samples were taken from sampling ports located on the top of the reactor, close to the reactor outlet. The experiments were performed at 70° C. by external heating and recirculation of hot water in the glass jacket.

During the experiments, whenever steady state was achieved, HRT or sugar concentrations were changed. The criteria for steady-state conditions were that all parameters must be held constant for at least five residence times. The reactor performance at different steady state was monitored by measuring the sugar and end-fermentation product concentrations. During the experiment, sterile syringes and needles were used to take the samples from the influent and effluent, and the samples were stored at −20° C. until analyzing. Effluent gas samples were taken to determine the carbon dioxide and hydrogen content.

Test for Contamination

A 1 ml sample was taken from the reactor and chromosomal DNA was purified using the DNA purification kit from A&A Biotech (Poland). PCR reactions were setup using the Pfu polymerase (MBI Fermentas, Germany) and the primers B-all 27F (SEQ ID NO:1; GAG TTT GAT CCT GGC TCA G) and B-all 1492R (SEQ ID NO:2; ACG GCT ACC TTG TTA CGA CTT), which anneal to bacterial rDNA. The fragments were purified using the Qiaex II kit from Qiagen, treated with PNK (MBI Fermentas), cloned into pBluescript SK+ (Stratagene) treated with CIAP (MBI Fermentas), and transformed into *Escherichia coli* Top10 (Invitrogen). 50 clones were picked and the inserts were amplified using B-all 27F and B-all 1492R primers. The resulting fragments were digested with AluI and MboI restriction enzymes (MBI Fermentas) and were run on a 3% agarose gel. Only one digestion pattern was found. Two fragments were sent for sequencing (MWG Biotech, Germany) and were identified as strain A10. PCR reactions were also run using primers Idhcw1 and Idhccw2 annealing to regions upstream and downstream of the lactate dehydrogenase respectively. Otherwise, the same reaction conditions as for the B-all primers, were used. The obtained fragments were cloned (as above), 26 were analysed by restriction fragment length polymorphism. Again, this resulted in only one pattern. Two fragments were sequenced.

Analytical Methods

The strains were grown in BA medium without antibiotics in batch for 24-48 hours as stated. The culture supernatants were analyzed for glucose, xylose, acetate, lactate and ethanol using an organic acid analysis column (Aminex HPX-87H column (Bio-Rad)) on a Hewlett Packard series 1100 HPLC at 65° C. with 4 mM $H_2SO_4$ as eluent.

Enzymes and Reagents

If not stated otherwise enzymes were supplied by MBI Fermentas (Germany) and used according to the suppliers' recommendations. PCR reactions were performed with a 1 unit:1 unit mixture of Taq polymerase and Pfu polymerase. Chemicals were of molecular grade and were purchased from Sigma-Aldrich Sweden AB.

16S rRNA Analysis

200 µl of BG1 overnight culture was harvested, treated for 2 minutes by microwave at maximum effect and used as a PCR template. A 1500 bp 16S rDNA was amplified by PCR using primers B1 (GAG TTT GAT CCT GGC TCA G) (SEQ ID NO:3) and B2 (ACG GCT ACC TTG TTA CGA CTT) (SEQ ID NO:4). The blunt ended PCR fragment was treated with polynucleotide kinase and cloned into SmaI digested and CIP (Calf Intestinal Phosphatase) treated pBluescript SK+ vector (Stratagene). 24 clones from the resulting DNA library were analysed by restriction enzyme fragment analyses using AluI, MboI and Hin6I restriction enzymes. 6 fragments were sent for sequencing at MWG-Biotech (Germany). The alignment was made using VectorNTi and the tree was drawn using the MEGA2 program (Kumar et al., 2001).

Analytical Techniques

The culture supernatants were analyzed for cellobiose, glucose, xylose, acetate, lactate and ethanol using an organic acid analysis column (Aminex HPX-87H column (Bio-Rad Laboratories, CA USA)) on HPLC at 65° C. with 4 mM $H_2SO_4$ as eluent. The ethanol and acetate measurements were validated using gas chromatography with flame ionization detection. Mixed sugars were measured on HPLC using a Phenomenex, RCM Monosaccharide (00H-0130-K0) column at 80° C. with water as eluent. Mannose and arabinose could not be distinguished using this setup and were therefore tested in separate cultures. Hydrogen was measured using a GC82 Gas chromatograph (MikroLab Aarhus, Denmark).

Construction of Idh Knock-Out Cassette

The final knock-out construct, p3CH contains 1) a DNA fragment upstream of the 1-Idh gene of BG1, amplified using primers Idhup1F (SEQ ID NO:5; 5'-TTCCATATCTG-TAAGTCCCGCTAAAG) and Idhup2R (SEQ ID NO:6; 5'-ATTAATACAATAGTTTTGACAAATCC), 2) a gene encoding a highly thermostable kanamycin resistance amplified from plasmid pUC18HTK (Hoseki et al., 1999. *J. Biochem. (Tokyo)*. 126(5), 951-956), and 3) a DNA fragment downstream of the 1-Idh gene of BG1, amplified using primers Idhdown3F (SEQ ID NO:7; 5'-ATATAAAAAGTCA-CAGTGTGAA) and Idhdown4R (SEQ ID NO:8; 5'-CAC-CTATTTTGCACTTTTTTTC). The plasmid p3CH was linearized and electroporated into BG1.

Construction of Hydrogenase Antisense Construct

The DNA fragment SEQ ID NO:9 containing the hydrogenase A antisense cassette was inserted into p3CH.

Construction of pfor Knock-Out Cassette

The final knock-out construct, pPF contains 1) a DNA fragment upstream of the 1-Idh gene of BG1, amplified using primers pforup1F (SEQ ID NO:10; 5'-GAGGATTTAA-GAAGGGGAGTTGG) and pforup2R (SEQ ID NO:11; 5'-ATTTCATCTCCCCCTGGATAAAG), 2) a gene encoding a highly thermostable kanamycin resistance amplified from plasmid pUC18HTK (Hoseki et al., 1999, *J. Biochem. (Tokyo)*. 126(5), 951-956), and 3) a DNA fragment downstream of the I-Idh gene of BG1, amplified using primers pfordown3F (SEQ ID NO:12; 5'-CGAGAGCTGATTC-CCACGAAGA) and pfordown4R (SEQ ID NO:13; 5'-CA-GACTACTACAACTGGATCTAGC). The plasmid p3 PF was linearized and electroporated into BG1.

Electroporation of BG1.

All handling, except for the electroporation event, was performed under anaerobic conditions. For preparation of competent cells, 150 ml BA amended with 2 g/l yeast extract and 5 g/l xylose was inoculated with a fresh ON culture of BG1 to an OD578 of 0.1 and incubated at 70° C. At OD578=0.5 the cells were chilled on ice, harvested (3500 rpm, 35 min, 4° C.) and resuspended in 10 ml cold EP buffer (0.3M sucrose, 10% glycerol, 3.20 mM $Na_2S$, pH 7, flushed with sterile $N_2$ gas). The wash was repeated and finally the pellet was resuspended in 4 ml EP-buffer without $Na_2S$. The cells were stored at −80° C. in aliquots. 0.2 ml of competent cells were transferred to electroporation cuvettes (0.1 cm electrode gap) containing 2 μg of linearized plasmid DNA and subjected to a pulse of 25 μF, 500 ohm, and 2.0 kV. The cells were transferred to anaerobic serum bottles containing 10 ml BA medium with 2 g/l yeast extract. The electroporated cells were allowed to recover at 70° C. for 16 hours. They were then diluted 10 fold into BA medium containing 35 μg/ml kanamycin. After 24 hours, the transfer into kanamycin containing medium was repeated and the culture was grown for 24 hours at 70° C. Using the Hungate technique (Bryant MP, 1972, *American Journal of Clinical Nutrition* 25, Hungate R. E., 1969. *In methods in Microbiology*, Norris, J. R. and D. W. Ribbons (Eds.). Academic Press, Inc. New York, pp: 117-132) 0.5 ml of culture was transferred to roll tubes with 35 μg/ml of kanamycin. After 2 days of incubation at 70° C., colonies were picked and inoculated in BA medium without antibiotics. Chromosomal DNA was purified from 4 individual recombinant clones and from wt BG1. A 2.1 kb fragment was amplified from the chromosomal DNA using primers Idhcw1 and Idhccw2 annealing just upstream and just downstream of the ldh gene respectively. These fragments were analyzed by restriction enzyme digests and were sequenced. PCR reactions using internal I-Idh primers only yielded products when wt BG1 was used as template.

Northern Blot Analysis

RNA was purified from 50 ml of exponentially growing *Thermoanaerobacter* cells using the Total RNA kit from A&A Biotechnology (Poland) as recommended by the supplier. 5 μg of total RNA was run in 1% agarose gels containing 80 mM Guanidine thiocyanate (mRNA blots) or 5% denaturing acrylamide gels (antisense blots). Blotting was performed using the TurboBlotter system (Scleicher & Schuell Bio-Science GmbH, Germany) as recommended. Hybridization was performed using the Ultrahyb solution from Ambion, Inc. (TX, USA) and washing was according to standard procedures (Ausubel et al., 1997. *Current Protocols In Molecular Biology*, John Wiley & Sons, Inc.). The sense and antisense probes were transcribed from pSKPhydD (The same hydD fragment used in the antisense construct, but without promoter and terminator sequences, inserted into the MCS of pBluescript SK+ (Invitrogen)) using labelled α-$P^{32}$CTP.

Yield and Carbon Recovery

Theoretical maximum yields and carbon recoveries were calculated based on the following reactions (ATP and NAD (P)+conversions are not included):

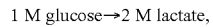

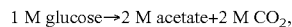

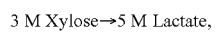

The theoretical maximum yields of ethanol from glucose and xylose are therefore 2 and 1.67 moles per mole respectively.

Carbon recoveries were calculated as:

$$\frac{3 \times (\text{mM lactate} + \text{mM acetate} + \text{mM ethanol produced})}{n \times (\text{mM substrate consumed})} \times 100\%$$

where n is 5 for xylose and 6 for glucose.

Example 1

16S Analysis of BG1

A library of 1500 bp 16S rDNA fragments from strain BG1 was constructed and analysed by restriction fragment length polymorphism analysis for different sequences. Only one digestion pattern was found and 6 clones were sequenced. The six sequences were identical and DNA homology search placed strain BG1 in the group of *Thermoanaerobacter mathranii*, which now consist of strains A3 and BG1. The 16S rDNA sequence of BG1 is shown in the sequence list as SEQ ID NO:14. Except for seven unsequenced positions in the GenBank (Benson et al., 2005) sequence of strain A3, the two strains have identical 16S rDNA sequences. As FIG. 1 shows, the closest other relatives are *Thermoanaerobacter thermocopriae* (98% identity), *Thermoanaerobacter acetoethylicus* (95%) and *Thermoanaerobacter italicus* (95%). BG1 is closely related to *Thermoanaerobacter mathranii* strain A3 (Larsen et al., 1997). This places BG1 in cluster V of the Clostridia as previously described (Collins et al., 1994). Although the strains are closely related, they are very different when it comes to tolerance to hemicellulosic hydrolysates. A3 could only grow in up to 40% wheat straw hydrolysate (of 60 g/l dry weight of wheat straw supplemented with xylose) while BG1 can grow and produce ethanol from undiluted hydrolysate with no addition of sugar or enzymes. Furthermore, strain A3 is reported not to be able to grow on galactose (Larsen et al., 1997), whereas BG1 grows nicely and produces primarily ethanol with galactose as the sole carbon source (data not shown).

Example 2

Fermentation Products of BG1

BG1 was grown anaerobically in batch for 24 hours with 27 mM xylose as the sole carbon source (FIG. 2). In the first four hours of fermentation, almost equal amounts of acetate and ethanol were produced. Between 4 and 6 hours of growth, ethanol production increased relative to acetate, and in the late exponential phase or in stationary phase, almost exclusively ethanol was produced. Only a minor amount of lactate was produced throughout the experiment. Hydrogen production seemed to follow the production of acetate with approximately equimolar amounts of the two compounds produced.

Example 3

Temperature, pH and Ethanol Tolerance of BG1

As can be seen from FIG. 3, the temperature optimum of strain BG1 is around 70° C., which is the same as the temperature of the hot spring from which BG1 was isolated. BG1 was found to grow in the pH range from pH=5.0 to 7.5. The product formation at different pH values of the culture medium was tested in batch experiments. As FIG. 4 shows, ethanol production was favoured in the pH range from 6.5 to 7.5, whereas lactate production was predominant at a lower pH. The optimal yield of ethanol was 1.15 mM ethanol/mM xylose at pH=6.5 and pH=7.5. At pH 5.5 the ethanol yield was 0.44 mM/mM. This corresponds to 69% and 26% of the theoretical maximum yield respectively.

Ethanol tolerance is of major importance for ethanol production. The product formation was investigated at elevated exogenous ethanol concentrations. As shown in FIG. 5, ethanol yields dropped dramatically at increased ethanol concentrations. At 0% initial ethanol in the medium, the yield was 1.05 mM ethanol/mM xylose consumed, whereas at 2.8% ethanol it was 0.31 mM/mM. This decrease in ethanol production was primarily due to increased lactate production (6.4 fold increase), but acetate production also increased by 40%. Apparently no other major products are formed, since carbon recoveries calculated from acetate, ethanol, lactate yields are in the range of 92-99% at all concentrations.

Example 4

BG1 Co-Fermentation of Hemicellulose Sugars

Simultaneous uptake and metabolism of different sugars is a desired but not very common trait for microorganisms used for ethanol production. BG1 was tested in batch on two different sugar mixtures, each containing four different hemicellulose sugar monomers, to study if the mixed monomers can be metabolized simultaneously (FIG. 6). Mannose and arabinose could not be distinguished in our HPLC setup and were therefore tested in separate mixtures. As can be seen from FIG. 6, a simultaneous degradation of all added sugars was observed between 6 and 8 hours of growth. The degradation rate of xylose was as high as that of glucose, although the onset of xylose degradation was slightly delayed. Galactose and arabinose were the last to be degraded, and the rate of degradation was slower than both the glucose and xylose rates. The rate of mannose degradation was the fastest observed, but again, the onset of degradation was delayed compared to glucose.

Example 5

BG1L1 and BGL2: Deletion of the I-Idh Gene from BG1

To prevent the formation of lactate, the L-LDH of BG1 was deleted. The purified pKHFr3rev plasmid, containing the thermostable kanamycin resistance gene flanked by the regions upstream and downstream from Idh, was linearized and electroporated into BG1, and positive recombinants were selected using the thermostable kanamycin resistance gene. Several independent clones were isolated and verified by PCR. PCR products from two clones were subsequently sequenced and were found to contain the kanamycin resistance cassette instead of the lactate dehydrogenase gene as expected. The two mutant strains were named BG1L1 and BG1L2.

Figure 7:
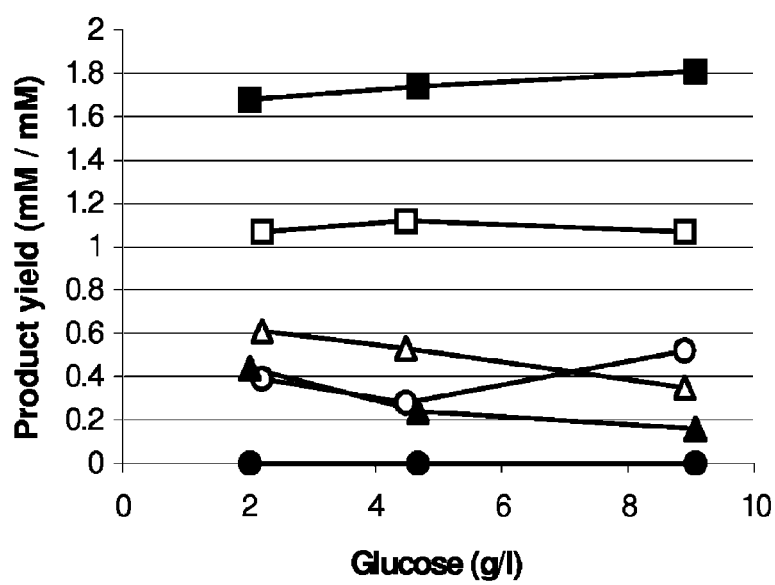

The wt BG1 strain and the two strains BG1L1 and BG1L2 were grown on different concentrations of glucose and xylose to test their ethanol production performance (FIGS. 7 and 8). For simplicity only BG1L1 is shown, but the parallel strain, BG1L2, showed very similar results and even had a slightly higher maximum yield on xylose than BG1L1.

As can be seen from FIGS. 7 and 8, the product distribution is greatly changed in the mutant. No detectable lactate is produced using either glucose or xylose as substrate, confirming the deletion of the lactate dehydrogenase gene. It also shows that the Idh gene described here is either the only Idh gene in BG1 or the primary one. The wild type BG1 strain responds to increased substrate concentration by increasing lactate production, especially when grown on xylose. A corresponding lower ethanol and acetate production is seen. The acetate production is constant or lower at higher sugar concentrations and, since it cannot produce lactate, a constant high or increasing ethanol production is seen. The ethanol yields are significantly improved in the mutant: On glucose, yields of 84-91% of the theoretical maximum are seen in BG1L1 as compared to 51-56% in the wt strain. On xylose the ethanol yields of BG1L1 and BG1 wt are 76-80% and 40-63% respectively. Carbon recoveries were between 91 and 106% (FIGS. 7B and 8B). Recoveries above 100% probably arise from metabolism of yeast extract components.

Figure 9:
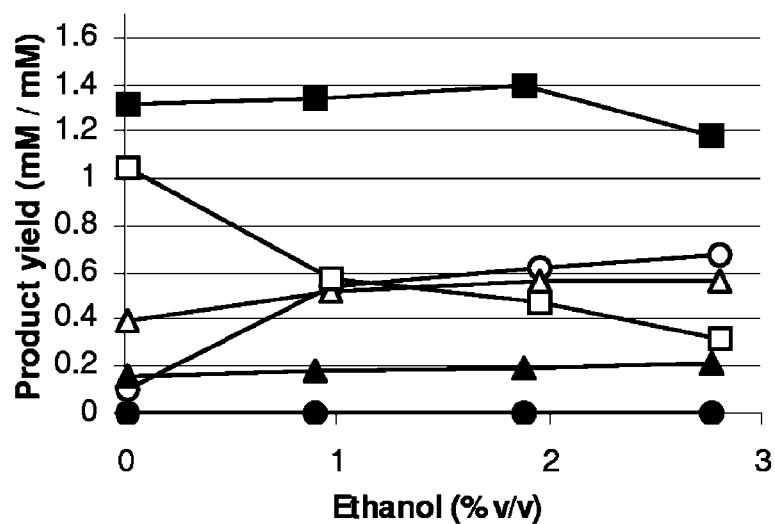

FIG. 9 shows the ethanol production of BG1 compared to BG1L at increasing concentrations of ethanol in the medium. The wt BG1 strain responds to increased ethanol concentrations in the medium by increasing lactate production dramatically. Acetate production increases around two fold. The ethanol yield decreases to only 20% of the maximum theoretical yield when 2.8% (v/v) ethanol is added. In BG1L, there is no lactate production and the production of acetate does not increase significantly at higher ethanol concentrations. As a result, the ethanol yield is high at all concentrations of ethanol in the medium. In fact, the highest yield measured is 84% of the theoretical maximum at 1.95% of ethanol added and at 2.8% of ethanol the yield is still 72%. Carbon recoveries were between 84 and 99% (FIG. 9B). The experiment was repeated with the independent clone BG1L2 with similar results.

Example 6

Continuous Fermentation of Sugars Using BG1L1

The potential of using immobilized thermophilic anaerobic bacteria for continuous ethanol fermentation was investigated in a lab-scale fluidized bed reactor operated at 70° C. (FIG. 10). The effect of hydraulic retention time (HRT) on ethanol production and productivity was examined at a feed stream with 10 g/l xylose. Product concentrations and xylose conversion were almost unaffected by gradually decreased HRT from 8 to 1 hour. Sugar conversion was higher than 97.8% yielding 0.33 g-ethanol/g-initial sugars and ethanol productivity gradually increased from 0.43 to 3.34 g/l/h. The second experiment was performed to investigate the co-fermentation of glucose and xylose. Both sugars were simultaneously and effectively converted to ethanol with sugar utilization higher than 90.6% at sugar mixtures up to 54 g/l. At these sugar concentrations, the ethanol production increased gradually and the maximum ethanol concentration achieved was 15.35 g/l. Ethanol yields were 0.28-0.40 g-ethanol/g-initial sugars. The maximum ethanol productivity obtained was 1.1 g/l/h at HRT of 8 hours and 30 g/l sugars. This study demonstrated that active immobilized cell culture of thermophilic anaerobic bacteria was possible. The reactor was operated continuously for 140 days with no contamination and showed good long-term performance.

Example 7

Continuous Fermentation of Steam Exploded Wheat Straw Using BG1L1

Steam exploded wheat straw hydrolysate (SEWS) was prepared by steam explosion followed by enzymatic hydrolysis (using Celluclast and Novozyme188 provided by Novozymes A/S) to release the constituent sugars, glucose and xylose. SEWS was provided by ELSAM, DK. The hydrolysate had dry matter content of 23% (DM), and glucose and xylose were, 57 g/l and 30 g/l, respectively. To counteract bacterial contamination, the SEWS hydrolysate medium was heated up to 121° C. for 1 min. Two SEWS suspensions were prepared by addition of respective volume of water given the desired concentrations of 7.5% and 15% DM corresponding to glucose-xylose mixtures of 12 and 43 g/l, respectively (FIG. 11). Despite, the SEWS medium was both sterilized and undetoxified, strain BG1L1 was capable as well of co-fermenting glucose and xylose efficiently with relatively high ethanol yield of 0.39-0.4 g/g (FIG. 12). Glucose was completely utilized (>98%) for both tested SEWS suspensions, whereas xylose conversion decrease from 99% to 80% at 15% (DM) SEWS, however, overall sugar conversion was higher than 90%. Acetate was the main by-product and remained relatively low during the entire fermentation (0.07-0.08 g/g) (FIG. 12).

In all these fermentations, only minor amounts of lactate were produced, as expected since the strain is a lactate dehydrogenase deficient mutant.

During both experiments lasting for approximately 140 days, the reactor was checked regularly for contamination by purifying chromosomal DNA from reactor samples, and no other species than BG1L1 were found. The deletion of the lactate dehydrogenase was also found to be stable as shown by sequencing of the lactate dehydrogenase region.

Example 8

Continuous Fermentation of Acid Pre-Treated Corn Stovers Using BG1L1

Corn stover hydrolysate (PCS), prepared by dilute sulfuric acid hydrolysis, was provided by the National Renewable Energy Laboratory (Golden, Colo., USA). The hydrolysate had a total solids (TS) content of 30% (wt), and xylose, glucose and acetic acid concentrations were 67 g/l, 15 g/l and 14 g/l, respectively. Corn stover hydrolysate in concentrations of 2.5%-15% TS was used. Because of the low total sugar concentration in the hydrolysate suspensions of 2.5% and 5% TS, extra 5 g/l xylose was added to these suspensions to prevent eventual process problems caused by the relatively low sugar content.

With PCS hydrolysate concentrations in the range of 2.5-10% TS, ethanol production increased gradually and relatively high and stable ethanol yields in a range of 0.41-0.43 g/g were obtained (FIG. 15). Almost complete sugar utilization (higher than 95%) was achieved for PCS of 2.5-7.5% TS, whereas at 10% (TS), the sugar conversion decreased to appr. 85% (FIG. 16). At a PCS concentration of 15% TS, sugar conversion was 70% and relatively high ethanol yields of close to 0.35 g/g was obtained. The lower sugar conversion at 15% (TS) PCS (FIG. 13) compared to other hydrolysate concentrations might be attributed to the growth and product inhibition caused by negative combination effect of high concentrations of acetate, other inhibitors present in the hydrolysate and salt accumulation resulted from based added for pH control (Lynd et al, 2001. *Biotechnology Progress* 17(1), 118-125; Palmqvist, E. and Hahn-Hägerdal B. 2000, *Bioresource technology* 74(1), 25-33; Zalvidar, J et al. 2001, *Applied Microbiology and Biotechnology* 56(1-2), 17-34). However, the low ethanol yield at PCS of 15% TS (FIG. 15) was probably due to higher ethanol evaporation than expected, since the carbon recovery was low (CR<0.9).

Acetate production increased from approximately 1 to 3.5 g/l (FIG. 14). However, because of high initial acetate concentrations (appr. 1-7 g/l) in the feed stream, a rather high concentration of nearly 10 g/l acetate was present in the effluent, which is significant with regard to the inhibitory effect of acetic acid to the fermentation. These results clearly show the high tolerance of the organism towards metabolic inhibitors present in undetoxified PCS.

Example 9

BG1PF: A Lactate Producing Mutant of Strain BG1

A strain derived from BG1 was made by integration of the DNA fragment shown in FIG. 20 into the chromosome of BG1. The purified ppta32K plasmid, containing the thermostable kanamycin resistance gene flanked by the regions upstream and downstream from pfor, was linearized and electroporated into BG1, and positive recombinants were selected using the thermostable kanamycin resistance gene. Several independent clones were isolated and verified by PCR. PCR products from two clones were subsequently sequenced and were found to contain the kanamycin resistance cassette instead of the pfor genes as expected.

Five independent clones of BG1PF were grown in batch for two days with 5 g/l xylose as carbon source. As can be seen from FIG. 21, a complete shift in metabolism is seen, and production of lactate is now the major product of fermentation.

Example 10

BG1H1: A BG1 Mutant with Increased Hydrogen Production Constructed by Down-Regulation of Uptake Hydrogenase Hydrogenases can be involved in both production and in uptake of hydrogen. In BG1, two sequences with similarity known hydrogenases were found. One (hydA BG1) was 80.4% identical on the DNA level to the *Thermoanaerobacter tengcongensis* hydA gene and 91.8% identical on the amino acid level to the corresponding HydA protein. The HydA protein is one out of 4 subunits in a cytosolic NAD(H) dependent Fe-only hydrogenase of *T. Tengcongensis*. The NADH dependent hydrogenase activity is inhibited by high hydrogen partial pressure, whereas the aldehyde dehydrogenase and alcohol dehydrogenase activities are higher in *T. tengcongensis* grown at elevated $p(H_2)$. Similarly the ethanol production is almost abolished in fermenter cultures with low $p(H_2)$.

The second sequence in BG1 with similarity to hydrogenases was found to be 73% identical to the echE gene of *Thermoanaerobacter tengcongensis* and 76% identical to the EchE protein subunit of the Ech hydrogenase of *Thermoanaerobacter tengcongensis*. The Ech hydrogenase is a ferredoxin dependent [NiFe] hydrogenase found in the membrane fraction of *Thermoanaerobacter tengcongensis* extracts. Both *Thermoanaerobacter tengcongensis* hydrogenases are primarily hydrogen evolving enzymes.

In *Thermoanaerobacter* BG1, the primary product is ethanol both under high and low $p(H_2)$. It is therefore likely that it employs a different strategy for hydrogen and ethanol production.

The effect of downregulation of the two hydrogenases was studied by introducing cassettes for downregulation of echE and hydA expression into the chromosome of BG1. The basic construction of the cassettes is shown in FIG. 22. When the cassette is introduced into BG1, the lactate dehydrogenase gene is removed, and the promoter is activated. This results in the expression of a small transcript complementary to the hydA and echE containing mRNA respectively. This expression will in most cases result in lower levels of mRNA due to digestion of double stranded RNA.

The expression of the hydA antisense RNA and the corresponding downregulation of hydA mRNA was validated by Northern blots (FIG. 23). Total RNA was purified from BG1, transferred to a membrane and probed with probes complementary to hydA anti-sense RNA and mRNA respectively. The promoter used to express the anti-sense RNA has been shown to be repressed by glucose and induced in the presence of xylose. In accordance with this, the anti-sense is only seen during growth on xylose. The wild-type BG1 strain and the BG1L1 strain, in which ldh has been deleted, but no anti-sense is inserted, are also shown as controls. As expected, no hydA anti-sense RNA is seen in these strains. The transcript from the hydA operon is expected to be around 500 b in length. When a probe directed against the hydA containing mRNA is used, a band which migrates as approximately 6000-7000 b is seen. One to two smaller and more intense bands of approx 3000-4000 b are also seen, in particular when the cells are grown with xylose as the carbon source. The smallest band is probably a cross-hybridization to 16S rRNA. The RNA corresponding to the 3-4000 b RNA varies greatly in intensity. The level of this species is much higher during growth on xylose as compared to glucose and higher in the strain deleted for the lactate dehydrogenase as compared to the wild-type. When grown on glucose, the levels of this band is equal in BG1L1 and BG1H1, while during growth on xylose it is much more intense in the strain where no anti-sense is expressed. This corresponds nicely to the expression of the anti-sense RNA expression in the upper panel.

As FIG. 24 shows, the BG1H1 produce more acetate, more hydrogen, and less ethanol than the control strains. This indicates that the HydABCD hydrogenase of BG1 is involved in hydrogen uptake, rather than production as it was shown for *T. tengcongensis*. As NAD(P)H is needed for the reduction of acetylCoA to acetaldehyde and acetaldehyde to ethanol, it is likely that the HydABCD hydrogenase is involved in the reduction of these cofactors using hydrogen. Both acetate and hydrogen are valuable products and strain BG1H1 may therefore be preferred if a higher hydrogen and acetate production is a target.

REFERENCES

Benson, D. A., Karsch-Mizrachi, I., Lipman, D. J., Ostell, J., and Wheeler, D. L. (2005). GenBank. Nucleic Acids Res. 33 *Database Issue*, D34-D38.

Bryant, F. O. (1991). Characterization of the fructose 1,6-bisphosphate-activated, L(+)-lactate dehydrogenase from *Thermoanaerobacter ethanolicus*. J Enzyme Inhib. 5, 235-248.

Burdette, D. S., Jung, S. H., Shen, G. J., Hollingsworth, R. I., and Zeikus, J. G. (2002). Physiological function of alcohol dehydrogenases and long-chain (C(30)) fatty acids in alcohol tolerance of *Thermoanaerobacter ethanolicus*. Appl. Environ. Microbiol. 68, 1914-1918.

Carreira, L. H., Ljungdahl, L. G., Bryant, F., Szulczynski, M., and Wiegel, J. (1982). Control of product formation with *Thermoanaerobacter ethanolicus*, enzymology and physiology. In Genetics of industrial micoorganisms, Y. Ikeda, ed. American Society for Microbiology, Washington D.C.), pp. 351-355.

Collins, M. D., Lawson, P. A., Willems, A., Cordoba, J. J., Fernandez-Garayzabal, J., Garcia, P., Cai, J., Hippe, H., and Farrow, J. A. (1994). The phylogeny of the genus *Clostridium*: proposal of five new genera and eleven new species combinations. Int J. Syst. Bacteriol. 44, 812-826.

Cook, G. M. (2000). The intracellular pH of the thermophilic bacterium *Thermoanaerobacter wiegelii* during growth and production of fermentation acids. Extremophiles 4, 279-284.

Dien, B. S., Nichols, N, N., O'Bryan, P. J., and Bothast, R. J. (2000). Development of new ethanologenic *Escherichia coli* strains for fermentation of lignocellulosic biomass. Appl Biochem. Biotechnol 84-86, 181-196.

Erbeznik, M., Dawson, K. A., and Strobel, H. J. (1998). Cloning and characterization of transcription of the xylAB operon in *Thermoanaerobacter ethanolicus*. J. Bacteriol. 180, 1103-1109.

Herrero, A. A. and Gomez, R. F. (1980). Development of ethanol tolerance in *Clostridium thermocellum*: effect of growth temperature. Appl. Environ. Microbiol. 40, 571-577.

Ho, N. W., Chen, Z., and Brainard, A. P. (1998). Genetically engineered *Saccharomyces* yeast capable of effective cofermentation of glucose and xylose. Appl. Environ. Microbiol. 64, 1852-1859.

Hueck, C. J. and Hillen, W. (1995). Catabolite repression in *Bacillus subtilis*: a global regulatory mechanism for the gram-positive bacteria? Mol. Microbiol. 15, 395-401.

Klinke, H. B., Thomsen, A. B., and Ahring, B. K. (2004). Inhibition of ethanol-producing yeast and bacteria by degradation products produced during pre-treatment of biomass. Appl. Microbiol. Biotechnol. 66, 10-26.

Kumar, S., Tamura, K., Jakobsen, I. B., and Nei, M. (2001). MEGA2: molecular evolutionary genetics analysis software. Bioinformatics. 17, 1244-1245.

Lamed, R. and Zeikus, J. G. (1980). Ethanol production by thermophilic bacteria: relationship between fermentation product yields of and catabolic enzyme activities in *Clostridium thermocellum* and *Thermoanaerobium brockii*. J Bacteriol 144, 569-578.

Larsen, L., Nielsen, P., and Ahring, B. K. (1997). *Thermoanaerobacter mathranii* sp nov, an ethanol-producing, extremely thermophilic anaerobic bacterium from a hot spring in Iceland. Arch. Microbiol. 168, 114-119.

Lawford, H. G. and Rousseau, J. D. (2002). Performance testing of *Zymomonas* mobilis metabolically engineered for cofermentation of glucose, xylose, and arabinose. Appl Biochem. Biotechnol 98-100, 429-448.

Lovitt, R. W., Longin, R., and Zeikus, J. G. (1984). Ethanol-Production by Thermophilic Bacteria—Physiological Comparison of Solvent Effects on Parent and Alcohol-Tolerant Strains of *Clostridium-Thermohydrosulfuricum*. Appl. Environ. Microbiol. 48, 171-177.

Lovitt, R. W., Shen, G. J., and Zeikus, J. G. (1988). Ethanol-Production by Thermophilic Bacteria—Biochemical Basis for Ethanol and Hydrogen Tolerance in *Clostridium-Thermohydrosulfuricum*. J. Bacteriol. 170, 2809-2815.

Lynd, L. R. (1989). Production of ethanol from lignocellulosic materials using thermophilic bacteria. Critical evaluation of potential and review. In Advances in biochemical engineering/Biotechnology, A. Fiechter, ed. (New York: Springer Verlag), pp. 1-52.

Rani, K. S, and Seenayya, G. (1999). High ethanol tolerance of new isolates of *Clostridium thermocellum* strains SS21 and SS22. World J. Microbiol. Biotechnol. 15, 173-178.

Rani, K. S., Swamy, M. V., Sunitha, D., Haritha, D., and Seenayya, G. (1996). Improved ethanol tolerance and production in strains of *Clostridium thermocellum*. World J. Microbiol. Biotechnol. 12, 57-60.

Saddler, J. N and Chan, M. K. H. Conversion of pretreated lignocellulosic substrates to ethanol by *Clostridium thermocellum* in mono- and co-culture with *Clostridium thermosaccharolyticum* and *Clostridium thermohydrosulfuricum*. Can J Microbiol 30, 212-220. 1984.

Wiegel, J. and Ljungdahl, L. G. *Thermoanaerobacter ethanolicus* gen. nov., spec. nov., a new, extreme thermophilic, anaerobic bacterium. Arch Microbiol 128, 343-348. 1981.

The invention claimed is:

1. A mutant strain of *Thermoanaerobacter mathranii* strain BG1 (DSMZ Accession number 18280), wherein one or more genes have been inserted, down-regulated or inactivated.

2. A mutant strain according to claim 1, wherein a gene encoding lactate dehydrogenase (LDH) (EC 1.1.1.27) has been down-regulated or inactivated.

3. A mutant strain according to claim 2, wherein the gene encoding lactate dehydrogenase (LDH) (EC 1.1.1.27) has been inactivated by the deletion of said gene.

4. A mutant strain according to claim 2, wherein the gene encoding lactate dehydrogenase (LDH) (EC 1.1.1.27) has been down-regulated or inactivated by a mutation, deletion or insertion of one or more amino acids in said gene.

5. A mutant strain according to claim 2, which is BG1L1 (DSMZ Accession number 18283).

6. A mutant strain according to claim 1, wherein a gene encoding pyruvate ferredoxin oxidoreductase (EC 1.2.7.1) has been down-regulated or inactivated.

7. A mutant strain according to claim 1, wherein a gene encoding pyruvate ferredoxin oxidoreductase (EC 1.2.7.1) has been down-regulated or inactivated by a mutation, deletion or insertion of one or more amino acids in said gene.

8. A mutant strain according to claim 6 which is BG1PF1 (DSMZ Accession number 18282).

9. A mutant strain according to claim 1, wherein a gene encoding a hydrogenase or a hydrogenase subunit has been down-regulated or inactivated.

10. A mutant strain according to claim 9, wherein the gene encoding the hydrogenase or the hydrogenase subunit has been down-regulated or inactivated by a mutation, deletion or insertion of one or more amino acids in said gene.

11. A mutant strain according to claim 9, wherein the hydrogenase or the hydrogenase subunit is selected from the group consisting of [Fe]-hydrogenases and [NiFe]-hydrogenases (EC 1.6.5.3, EC 1.12.7.2, EC 1.12.99.6).

12. A mutant strain according to claim 9 which is BG1H1 (DSMZ Accession number 18281).

13. A mutant strain according to claim 1, wherein a gene encoding an acetate kinase (EC 2.7.2.1) has been down-regulated or inactivated by a mutation, deletion or insertion of one or more amino acids in said gene.

14. A mutant strain according to claim 1, wherein a gene encoding a phosphate acetyltransferase (EC 2.3.1.8) has been down-regulated or inactivated by a mutation, deletion or insertion of one or more amino acids in said gene.

15. A mutant strain according to claim 9, wherein the gene encoding the hydrogenase or the hydrogenase subunit is NuoE, NuoF, NuoG, EchB, EchC, EchD, EchE, or EchF.

16. A mutant strain according to claim 1, wherein one or more genes have been inserted.

17. A mutant strain according to claim 16, wherein said one or more inserted genes comprise a gene encoding a polysaccharase.

18. A mutant strain according to claim 17, wherein the polysaccharase is selected from the group consisting of cellulases (EC 3.2.1.4); beta-glucanases; xylanases; pectinases (EC 3.2.1.15); alpha-glucuronidase, alpha-L-arabinofuranosidase (EC 3.2.1.55), acetylesterase (EC 3.1.1.-) acetylxylanesterase (EC 3.1.1.72), alpha amylase (EC 3.2.1.1), beta-amylase (EC 3.2.1.2), glucoamylase (EC 3.2.1.3), pullulanase (EC 3.2.1.41), beta-glucanase (EC 3.2.1.73), hemicellulase, arabinosidase, mannanases; pectin hydrolase, polygalacturonase (EC 3.2.1.15), exopolygalacturonase (EC 3.2.1.67) and pectate lyase (EC 4.2.2.10).

19. A mutant strain according to claim 18, wherein the beta-glucanases include glucan-1,3 beta-glucosidases (exo-1,3 beta-glucanases, EC 3.2.1.58), 1,4-beta-cellobiohydrolase (EC 3.2.1.91) and endo-1,3(4)-beta-glucanases (EC 3.2.1.6).

20. A mutant strain according to claim 18, wherein the xylanases include endo-1,4-beta-xylanases (EC 3.2.1.8) and xylan 1,4-beta-xylosidase (EC 3.2.1.37).

21. A mutant strain according to claim 18, wherein the mannanases include mannan endo-1,4-beta-mannosidase (EC 3.2.1.78) and mannan endo-1,6-alpha-mannosidase (EC 3.2.1.101).

22. A mutant strain according to claim 16, wherein said one or more inserted genes comprise a gene encoding a pyruvate decarboxylase (EC 4.1.1.1).

23. A mutant strain according to claim 16, wherein said one or more inserted genes comprise a gene encoding an alcohol dehydrogenase (EC 1.1.1.1, EC 1.1.1.2, EC 1.1.1.71, EC 1.1.99.8).

24. A mutant strain according to claim 1, wherein a gene encoding an alcohol dehydrogenase has been upregulated.

* * * * *

UNITED STATES PATENT AND TRADEMARK OFFICE
CERTIFICATE OF CORRECTION

PATENT NO.       : 8,512,714 B2                                    Page 1 of 1
APPLICATION NO.  : 12/301687
DATED            : August 20, 2013
INVENTOR(S)      : Mikkelsen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 922 days.

Signed and Sealed this
Fifteenth Day of September, 2015

Michelle K. Lee
*Director of the United States Patent and Trademark Office*